US012751708B2

(12) United States Patent
Otto et al.

(10) Patent No.: US 12,751,708 B2
(45) Date of Patent: Oct. 6, 2026

(54) FORCE MEASURING JOINT DISTRACTION LEVER

(71) Applicant: MAKO Surgical Corp., Weston, FL (US)

(72) Inventors: Jason Otto, Sioux Falls, SD (US); Mark Nadzadi, Batavia, OH (US); Radu Iorgulescu, Boca Raton, FL (US); Kevin Bechtold, Weston, FL (US); Hyosig Kang, Weston, FL (US)

(73) Assignee: MAKO SURGICAL CORP., Weston, FL (US)

( * ) Notice: Subject to any disclaimer, the term of this patent is extended or adjusted under 35 U.S.C. 154(b) by 49 days.

(21) Appl. No.: 18/807,423

(22) Filed: Aug. 16, 2024

(65) Prior Publication Data

US 2024/0398399 A1 Dec. 5, 2024

Related U.S. Application Data

(60) Continuation of application No. 17/575,188, filed on Jan. 13, 2022, now Pat. No. 12,082,800, which is a (Continued)

(51) Int. Cl.
*A61B 17/02* (2006.01)
*A61B 17/16* (2006.01)
(Continued)

(52) U.S. Cl.
CPC ............ *A61B 17/025* (2013.01); *A61B 17/16* (2013.01); *A61B 17/1675* (2013.01);
(Continued)

(58) Field of Classification Search
CPC .......... A61B 17/025; A61B 2017/0268; A61B 2090/064; A61B 34/20
See application file for complete search history.

(56) References Cited

U.S. PATENT DOCUMENTS 4,995,875 A 2/1991 Coes
5,431,653 A 7/1995 Callaway
(Continued)

FOREIGN PATENT DOCUMENTS

DE 20 2010 000 341 U1 5/2010
EP 2 011 442 A1 1/2009
GB 2 455 182 6/2009

OTHER PUBLICATIONS

International Search Report and Written Opinion for International Application No. PCT/US2015/032973, mailed Sep. 24, 2015, 14 pages.

(Continued)

*Primary Examiner* — Samuel S Hanna

(74) *Attorney, Agent, or Firm* — Foley & Lardner LLP

(57) ABSTRACT

A surgical system includes a joint distractor configured to apply a distraction force to a first bone to distract a joint, a tracking system configured to track relative poses of the joint distractor and the first bone of the joint in contact with the joint distractor, and a computing system. The computing system is programmed to receive information indicating the relative poses of the joint distractor rand the first bone of the joint, determine, using the relative poses of the joint distractor and the first bone of the joint, a characteristic of the distraction force, and cause, using the characteristic of the distraction force, an adjustment of the distraction force.

20 Claims, 13 Drawing Sheets

Related U.S. Application Data continuation-in-part of application No. 17/132,053, filed on Dec. 23, 2020, now Pat. No. 11,660,083, and a continuation-in-part of application No. 16/447,507, filed on Jun. 20, 2019, now Pat. No. 11,253,246, said application No. 17/132,053 is a division of application No. 14/724,381, filed on May 28, 2015, now Pat. No. 10,918,368.

(60) Provisional application No. 62/688,151, filed on Jun. 21, 2018, provisional application No. 62/004,015, filed on May 28, 2014.

(51) Int. Cl.
*A61B 34/20* (2016.01)
*A61B 17/00* (2006.01)
*A61B 90/00* (2016.01)

(52) U.S. Cl.
CPC ............... *A61B 2017/00115* (2013.01); *A61B 2017/0268* (2013.01); *A61B 34/20* (2016.02); *A61B 2090/064* (2016.02)

(56) References Cited

U.S. PATENT DOCUMENTS

| | | | |
|---|---|---|---|
| 6,558,392 | B1 | 5/2003 | Martini |
| 6,859,661 | B2 | 2/2005 | Tuke |
| 8,010,180 | B2 | 8/2011 | Quaid et al. |
| 8,162,951 | B2 | 4/2012 | Kaufman |
| 8,211,041 | B2 | 7/2012 | Fisher et al. |
| 8,337,508 | B2 | 12/2012 | Lavallee et al. |
| 8,516,907 | B2 | 8/2013 | Stein et al. |
| 9,351,850 | B2 | 5/2016 | Fischer et al. |
| 9,665,686 | B2 | 5/2017 | Van Vorhis et al. |
| 11,051,798 | B2 | 7/2021 | Plaskos et al. |
| 2007/0179626 | A1 | 8/2007 | De la Barrera et al. |
| 2007/0219561 | A1 | 9/2007 | Lavallee et al. |
| 2007/0244488 | A1 | 10/2007 | Metzger et al. |
| 2008/0262812 | A1 | 10/2008 | Arata et al. |
| 2009/0198240 | A1 | 8/2009 | Kaufman |
| 2010/0198275 | A1 | 8/2010 | Chana et al. |
| 2010/0217156 | A1 | 8/2010 | Fisher et al. |
| 2010/0249658 | A1 | 9/2010 | Sherman et al. |
| 2010/0250571 | A1 | 9/2010 | Pierce et al. |
| 2010/0326210 | A1 | 12/2010 | Stein et al. |
| 2010/0331737 | A1 | 12/2010 | Stein et al. |
| 2011/0319755 | A1 | 12/2011 | Stein et al. |
| 2012/0016427 | A1 * | 1/2012 | Stindel ............... A61B 17/8023 606/86 R |
| 2012/0232429 | A1 | 9/2012 | Fischer et al. |
| 2012/0330368 | A1 | 12/2012 | Dunn |
| 2013/0023795 | A1 | 1/2013 | Stein et al. |
| 2013/0079669 | A1 | 3/2013 | Stein et al. |
| 2013/0079670 | A1 | 3/2013 | Stein et al. |
| 2013/0079674 | A1 | 3/2013 | Stein et al. |
| 2013/0079675 | A1 | 3/2013 | Stein et al. |
| 2013/0079792 | A1 | 3/2013 | Stein et al. |
| 2013/0079884 | A1 | 3/2013 | Stein et al. |
| 2013/0102929 | A1 | 4/2013 | Haight et al. |
| 2013/0103038 | A1 | 4/2013 | Fischer et al. |
| 2013/0226036 | A1 | 8/2013 | Stein et al. |
| 2014/0188129 | A1 | 7/2014 | Kang |
| 2015/0342588 | A1 | 12/2015 | Bechtold et al. |
| 2017/0360512 | A1 | 12/2017 | Couture et al. |
| 2018/0008138 | A1 | 1/2018 | Thommen et al. |
| 2019/0008500 | A1 * | 1/2019 | Plaskos ................. A61B 34/10 |

OTHER PUBLICATIONS

June Okamoto, et al; 35th Annual Int Conf of the IEE EMBS, Robotic Tensor Device for Optimal Soft Tissue Balance in TKA , published Jul. 2013, Osaka, Japan: https://ieeexplore.ieee.org/stamp/stamp.jsp?tp=&arnumber=6611092.

* cited by examiner

FORCE MEASURING JOINT DISTRACTION LEVER

CROSS-REFERENCE TO RELATED APPLICATIONS

This application is a continuation of U.S. patent application Ser. No. 17/575,188, filed Jan. 13, 2022, which is a continuation-in-part of U.S. patent application Ser. No. 16/447,507, filed Jun. 20, 2019, which claims the benefit of and priority to U.S. Provisional Patent Application No. 62/688,151, filed Jun. 21, 2018; U.S. patent application Ser. No. 17/575,188 is also a continuation-in-part of U.S. patent application Ser. No. 17/132,053, filed Dec. 23, 2020, which is a divisional of U.S. patent application Ser. No. 14/724,381, filed May 28, 2015, which claims the benefit of and priority to U.S. Provisional Patent Application No. 62/004,015, filed May 28, 2014; all of which are incorporated by reference herein in their entireties.

BACKGROUND

The present invention relates generally to the field of surgical tools for use during planning and preparation of a joint replacement procedure, and more particularly to a force measuring lever for use during joint distraction.

Over time, as a result of disease, injury, or longevity of use, bones of a joint may degenerate, resulting in pain and diminished functionality. To reduce pain and restore functionality, a joint replacement procedure may be necessary. Examples of such procedures may be total or partial knee arthroplasty, total hip arthroplasty, or knee or hip resurfacing. In these procedures, portions of a patient's joint are replaced with artificial components. Particularly, a surgeon uses a surgical cutting tool to remove portions of bone to prepare the bone to receive a prosthetic device. Prior to resection of the bone, the surgeon plans bone preparation specific to the patient's anatomy, size, current state of the target joint, and several other factors in order to determine the portions of the bone that will be removed and replaced by one or more prosthetic components, as well as to determine proper positioning of the one or more prosthetic components.

One step of surgical planning for a partial knee resurfacing procedure involves a knee joint distraction, that is, forced separation of the distal femur from the proximal tibia. For partial knee resurfacing, this is intended to correct knee joint deformity and cause proper re-tensioning of the ligaments of the knee to determine a desired, post-procedure joint construction. In one exemplary method, prior to resection and prior to a creating a final implant plan, the knee joint deformity is corrected at multiple flexion positions or flexion angles by distracting the joint. An instantaneous six degree-of-freedom (DOF) position (i.e. the pose) of the femur with respect to the six DOF position of the tibia is captured at each of the multiple flexion positions. For example, a common flexion position is near full extension where the surgeon applies a valgus torque to the tibia when the leg is at approximately 5-10 degrees of flexion. The valgus torque corrects the limb alignment deformity and returns the ligaments to a proper tension state. Another common flexion position is 90 degrees flexion. With these two poses, the knee joint is in the desired post-resection final position. After collection of poses, bone resection, implant positioning, and implant characteristics are planned so as to maintain this relative alignment by making the femoral and tibial components contact (or be slightly gapped to allow for some laxity). Once the bone is resected at this desired plan and the trials and/or implants are secured to the bone, the leg will then be in the pre-resected posed positions.

A first technique currently used to apply a joint distraction force includes manually applying a valgus torque (for a varus knee) to the tibia portion of a patient's leg to pivot the knee joint about the contralateral compartment (lateral compartment for a varus knee). Another technique includes applying a distraction force using a common surgical osteotome by levering the osteotome off the front of the tibia and lifting the femur vertically. Similarly, joint distraction may be performed by placing shim-like spoons or gap sticks between the femur and tibia, or by using laminar spreaders to create the distance between the femur and the tibia.

However, for each of these techniques, the "proper" joint distraction force is subjective, varies from surgeon-to-surgeon, and is difficult for surgeons to learn. In addition, for the first technique described above, applying a valgus torque to the tibia for any pose after 30 degrees flexion is extremely difficult because the femur tends to rotate about the femoral head.

Other types of distractors include spring-based, electromechanical, or hydraulic opposing plate spreaders. However, these tend to be large and complex, and due to their size generally require at least some bone to be removed first (provisional resection) to accommodate the device's opposing plates. Yet another device is a force sensing shim. However, like the shim-like spoons or gap sticks, this device generally requires iteratively inserting the device into the joint with various thicknesses until the desired force is achieved, making it time consuming and cumbersome.

SUMMARY

According to one aspect, the present disclosure is directed to a joint distraction lever having a lever body having a handle portion and a working portion. The joint distraction lever includes a fulcrum extending from a bottom surface of the working portion of the lever body, and a distal tip, where the distal tip is raised above a top surface of the working portion of the lever body. The joint distraction lever also includes a force measurement device for measuring a distraction force applied at the distal tip during a distraction procedure for a joint, during which a torque is applied at the handle portion of the lever body. In addition, the joint distraction lever includes a force value output that indicates the distraction force applied at the distal tip.

According to another aspect, the present disclosure is directed to a method for applying a distraction force during a distraction procedure. The method includes providing a joint distraction lever comprising. The joint distraction lever has a lever body with a handle portion coupled to a working portion, a fulcrum extending from a bottom surface of the working portion of the lever body, and a distal tip that is raised above a top surface of the working portion of the lever body. The joint distraction lever also includes a force measurement device that measures the distraction force, and a force value output that indicates the distraction force applied at the distal tip. Further, the method includes inserting the joint distraction lever into a space between a first bone and a second bone of a joint, and applying a force to the handle portion of the joint distraction lever. In addition, the method includes measuring the distraction force via the force measurement device, and outputting the measured distraction force by the force value output.

The invention is capable of other embodiments and of being practiced or being carried out in various ways. Alternative exemplary embodiments relate to other features and combinations of features as may be generally recited in the claims.

BRIEF DESCRIPTION OF THE FIGURES

The invention will become more fully understood from the following detailed description, taken in conjunction with the accompanying drawings, wherein like reference numerals refer to like elements, in which.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Figures 1, 2A, 2B:
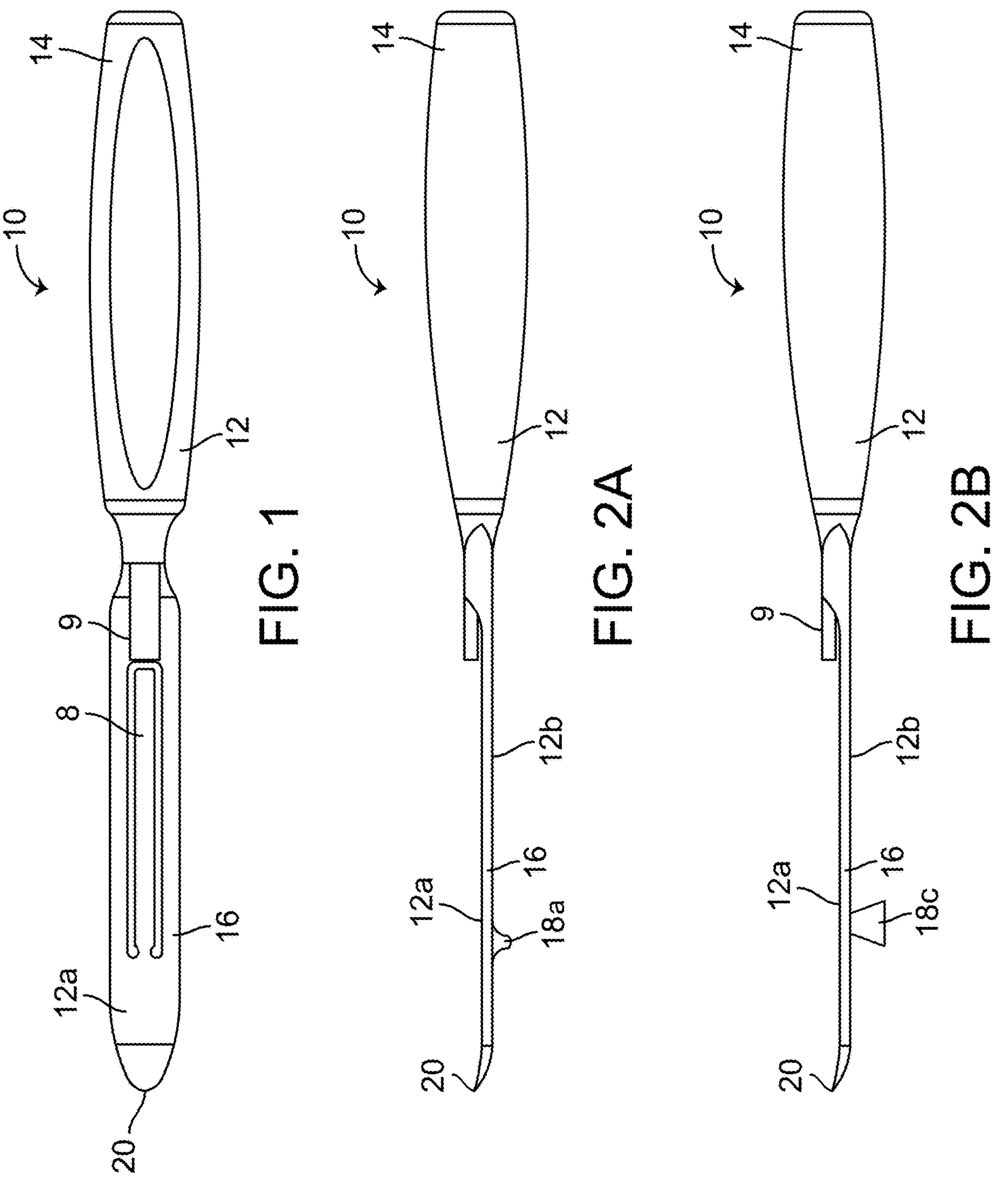
FIG. 1 is a top side view of a joint distraction lever according to a first exemplary embodiment.
FIG. 2A is a lateral side view of the joint distraction lever of FIG. 1.
FIG. 2B is a lateral side view of a joint distraction lever according to another exemplary embodiment.

Referring to FIGS. 1-3, a joint distraction lever is shown. In certain embodiments, the joint distraction lever is an osteotome 10. Though the present description will refer to the joint distraction lever as the osteotome 10, it is to be understood that the features disclosed herein may be used with and provided in a variety of lever-type devices, which are considered to be within the scope of the present disclosure. As shown in FIGS. 1-3, the various embodiments of osteotome 10 include a lever body 12 having a handle portion 14 and a working portion 16. A fulcrum 18 extends from a bottom face 12*b* of the working portion 16 of the lever body 12. At a distal end of lever body 12 there is provided a distal tip 20. Distal tip 20 is raised to extend above the top face 12*a* of the lever body 12. In the embodiments shown, the distal tip 20 curves upwardly from the working portion 16 at the distal end of the lever body 12.

The osteotome 10 preferably has a thin, narrow lever body 12 sized to be inserted into a pre-resection narrow joint space. The lever body 12 may be between 1-3 mm thick at the working portion 16, and in a preferred embodiment is no more than 2 mm thick. In some preferred embodiments, the thickness of the working portion 16 tapers towards the distal tip 20 to no more than 1 mm thick at the distal tip 20. The width of the working portion 16 may be between 10-22 mm wide to accommodate compartments of various sizes, and in a preferred embodiment is approximately 15 mm wide.

Figure 4:
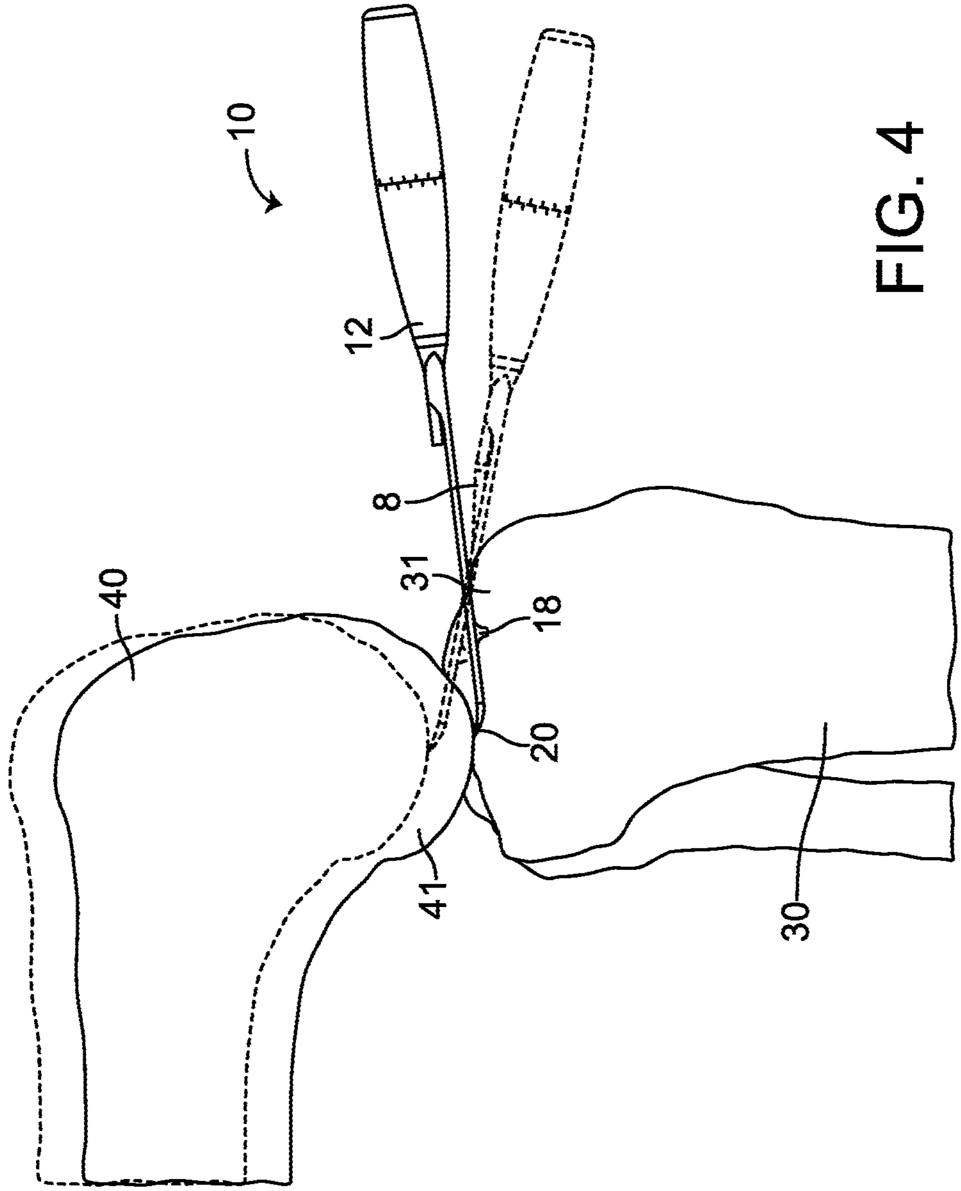
FIG. 4 depicts joint distraction of a patient's knee joint using the joint distraction lever of FIG. 1.
Figure 5:
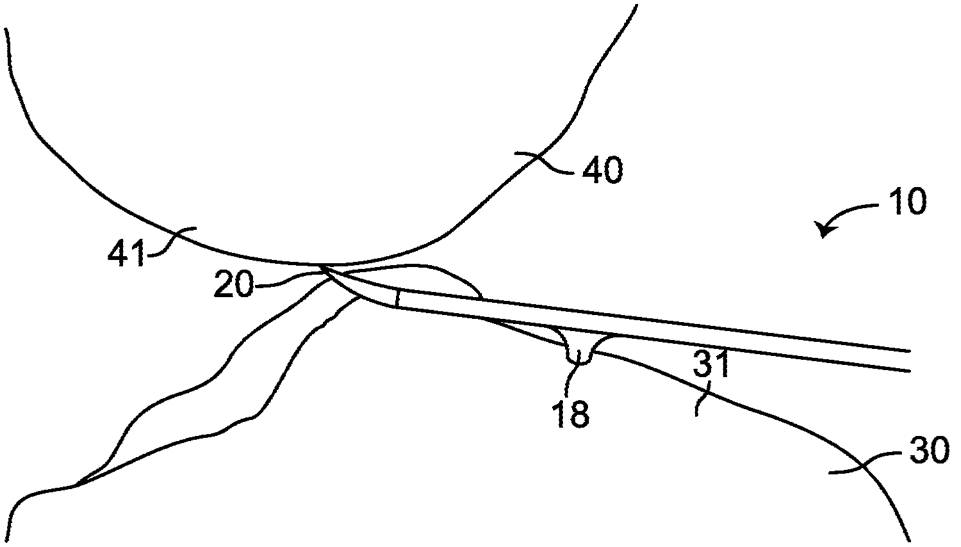
FIG. 5 depicts a closer view of joint distraction of a patient's knee joint using the joint distraction lever of FIG. 1.
Figure 6:
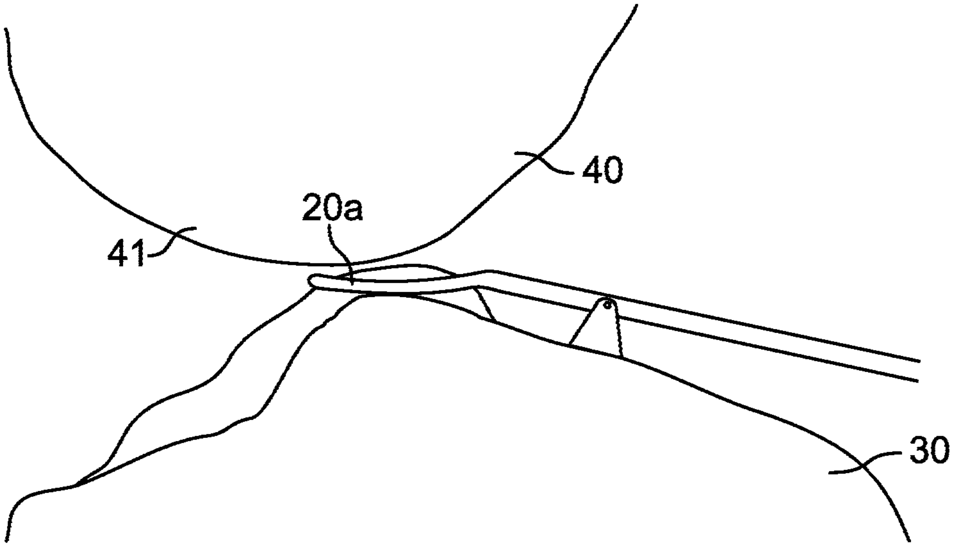
FIG. 6 depicts joint distraction of a patient's knee joint using a joint distraction lever according to another exemplary embodiment.

Referring to FIG. 4, it is shown that the fulcrum 18 is configured to rest on a first bone of a joint. The embodiments of the joint distraction device are depicted and described herein as being used in a knee joint, though it should be understood that the joint distraction device may be used in any joint that is suitable for a joint distraction procedure. Thus, in the figure, the fulcrum is shown resting on a tibial plateau 31 of a patient's tibia 30. This provides the support for the osteotome 10 and the point around which the torque is applied and the distraction force will be provided to the distal end of the patient's femur 40 through distal tip 20. As depicted in FIG. 4, as an external force is exerted on the handle portion 14 of the lever body 12, a torque is applied to the lever body 12 about the fulcrum 18. A resulting force is then applied at the distal tip 20 which causes the distraction of the joint, that is, for example, the separation of the first bone (tibia 30) from the second bone (femur 40).

The joint distraction device according to various embodiments is dependent on the force being applied at two known locations: the fulcrum 18 and the distal tip 20. To ensure that forces are being applied only at these two locations, the fulcrum 18 and the distal tip 20 project from the bottom face 12*b* and the top face 12*a*, respectively, of lever body 12 such that the lever body 12 does not inadvertently contact either bone of the joint.

Figure 3A:
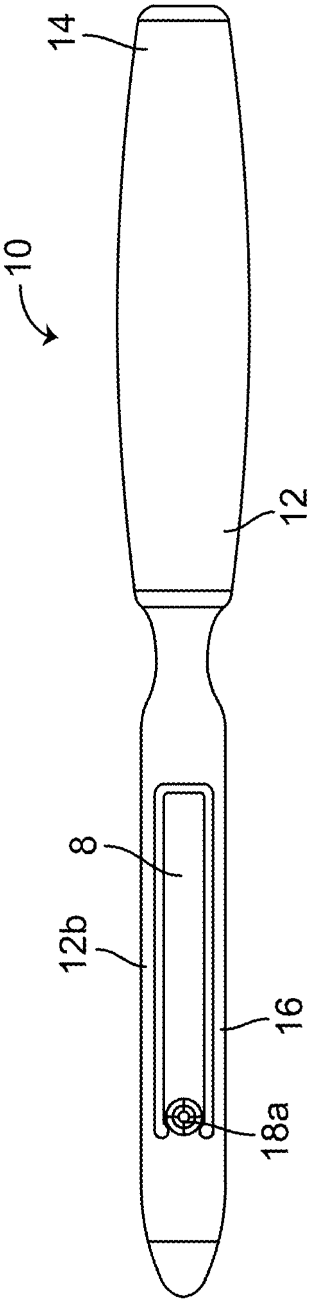
FIG. 3A is a bottom side view of the joint distraction lever of FIG. 1.

As such, the fulcrum 18 is designed to project from the bottom face 12*b* to a distance sufficient to prevent contact of the bottom face 12*b* with the tibia 30 during use. In a preferred embodiment, the fulcrum 18 extends proud of the lever body 12 by at least 2 mm, but may be anywhere between 1-3 mm proud of the lever body 12, or more. In certain embodiments, the widest portion of the fulcrum 18 is between 4-8 mm, and the thickest portion is between 1-2 mm. The fulcrum may be instrumented such that the fulcrum itself is configured to measure the load being applied at the fulcrum. In such an embodiment, an instrumented fulcrum can be attached to a standard osteotome to achieve certain features of the disclosed embodiments without further modification to force measuring aspects of the osteotome. As shown in the embodiment of FIGS. 2A and 3A, the fulcrum 18*a* shape may be somewhat tapered or sharp into a pointed tip to allow slight penetration into bone and/or cartilage to provide stability of the osteotome 10 during distraction and while the joint poses are being captured.

Figure 2C:
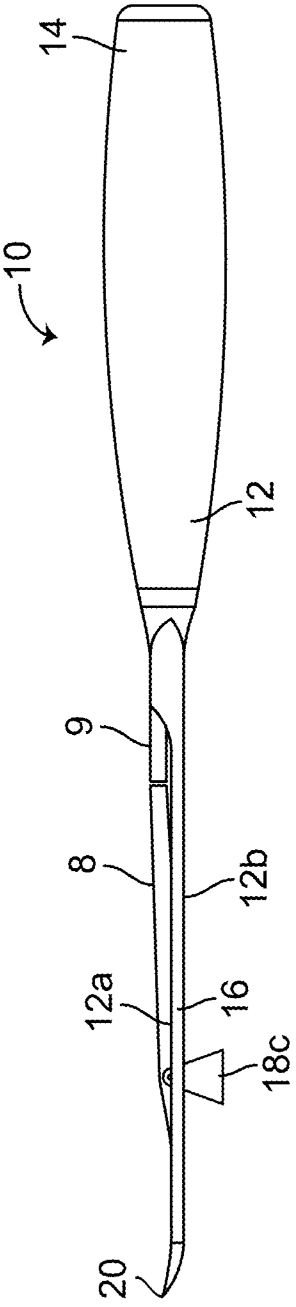
FIG. 2C is a second lateral side view of the joint distraction lever of FIG. 2B.
Figure 3C:
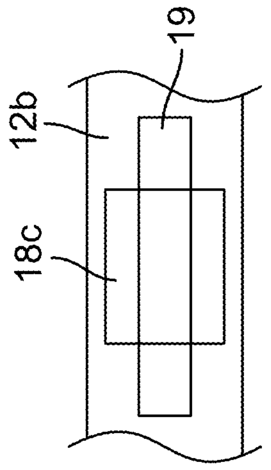
FIG. 3C is a bottom side view of the joint distraction lever of FIG. 2B.
Figure 3B:
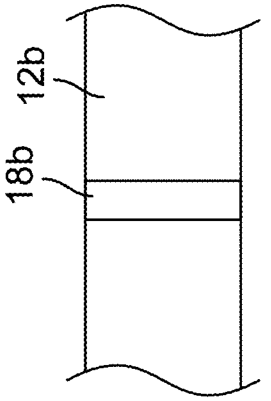
FIG. 3B is a bottom side view of a joint distraction lever according to another exemplary embodiment.

In the embodiment shown in FIGS. 2B, 2C, and 3C, the fulcrum is a triangular pad 18*c*. The triangular pad 18*c* may be connected to the lever body at a rotatable pivot joint. The triangular pad 18*c* provides greater surface in contact with the bone to minimize penetration into the bone when such penetration would be detrimental or undesirable. Though the pad shown in FIGS. 2B, 2C, and 3C is triangular, other configurations having a narrow top portion to form a portion of a pivot joint, and a wider bottom portion to contact the bone can be used to provide a pivot pad for pivoting of the lever body about the fulcrum. In other embodiments, such as that shown in FIG. 3B, the fulcrum is a linear fulcrum 18*b* extending laterally across the lever body 12. This embodiment also provides a greater surface area in contact with the bone and may also reduce the penetration of the fulcrum into the bone during use.

The distraction force, and thus the measurement of the distraction force applied through the distal tip 20 (to be discussed in detail below), is sensitive to fulcrum 18 to lift point (distal tip 20) distance. When the distance from the fulcrum 18 to the raised distal tip 20 is known or selected, which it will be when the joint distraction lever is used, the applied distraction force can be calculated. The fulcrum 18 to distal tip 20 distance may be fixed or may be variable and/or adjustable. In a fixed fulcrum to tip embodiment, the spacing may be between 10-25 mm. An adjustable distance embodiment may allow for a greater range of the fulcrum to tip distance. FIG. 3C depicts an embodiment wherein the fulcrum 18 to distal tip 20 distance can be adjusted by moving the pivot joint along slot 19 and securing it at a desired distance from distal tip 20. In certain preferred embodiments, the distance between the fulcrum 18 and the distal tip 20 is fixed at 20 mm. This distance is particularly useful for distraction of the knee joint, as it allows the fulcrum 18 to rest on the tibial plateau 31 of the tibia 30 and the distal tip 20 to be directly below the femoral condyle 41.

Referring to FIGS. 2 and 4-7, it is shown that the distal tip 20 projects above the top face 12*a* of the lever body 12. In the embodiments shown, the distal tip 20 of the working portion 16 curves upward to form distal tip 20. Again, in order that forces are applied to the bones of the joint only at the fulcrum 18 and distal tip 20, the distal tip 20 is configured such that the top face 12*a* of the lever body 12 does not contact the femur 40 during distraction of the joint. The raised distal tip 20 may stand 1-5 mm proud of the top face 12*a* of the lever body 12, and in a preferred embodiment is curved to be 4 mm proud of the lever body 12. As shown in the embodiment of FIGS. 2, 4, 5, and 7, the lever body 12 may taper towards the distal tip 20, such that distal tip 20 is pointed. The pointed tip, in a preferred embodiment, has a width of about 1 mm.

The profile of the lever body 12, particularly the distal tip 20, may take on various profiles, not limited to the pointed distal tip shown in the previous embodiments. In one exemplary configuration, such as that shown in FIG. 6, the distal tip 20 takes on the shape of a plate 20*a*. The shape may be slightly curved to fit with the outer surface of the bone. In some embodiments, the plate 20*a* at the distal tip is specifically configured for a particular bone or the anatomy of a particular patient. This configuration provides greater contact surface area for torque transmission efficiency as well as to reduce penetration of the bone being distracted. Other configurations of the distal tip may also be used in accordance with additional embodiments of the present invention.

The joint distraction lever may have a rotatable handle portion 14. The rotatable handle portion 14 may allow for a reduction in the amount of torque working laterally during joint distraction. For example, when distracting the knee joint, it is intended to provide the distraction force substantially parallel with the mechanical axis of the joint. However, the surgeon may not be able to achieve exact access and grip on the tool such that all forces are being applied in this direction. Some torque, instead, may be applied sideways on the joint while also being applied in parallel with the mechanical axis. The rotatable handle portion 14 may counteract some of the sideways torque applied by cooperating with the twisting that may occur on the handle when the force is applied at the handle portion 14.

The joint distraction lever, such as osteotome 10, is configured to measure and provide output related to the distraction force applied to the bone of the joint, such as the femur 40, by the distal tip 20 during a distraction procedure. The distraction force is measured by a force measurement device. The embodiment of FIG. 1 shows a mechanical force measurement osteotome. In this embodiment, the lever body 12 includes a cut out portion forming a cantilever beam 8. Upon application of an applied force, the cantilever beam 8 tilts upward (as depicted in FIGS. 2C and 4). The cantilever beam 8 may be used to determine the applied force based on its relationship with a reference feature. For example, as shown in FIGS. 2C and 4, the cantilever beam 8 may move towards alignment with tab 9 extending from the handle portion 14. The joint distraction lever can be configured such that alignment of the cantilever beam is with the tab 9 indicates a predetermined force value.

Another non-electronic configuration for determining the distraction force applied at the distal tip 20 is an analog torque wrench that is configured to apply a set specific torque to the wrench body or, particularly, lever body 12. Analog graduations of torque settings may be available, and once determined and set, the lever body 12 will be configured to apply a torque and thus cause a distraction force at the distal tip 20 until a predetermined, desired force is applied. When the preset torque has been met, the wrench, or lever, is configured to indicate that the preset torque has been reached, or otherwise prevent further torque from being applied through the lever body.

In another exemplary embodiment, the force measurement device is a strain gauge. One or more strain gauges may be coupled with the lever body 12 and configured to receive an input voltage provided by a power source. In certain embodiments, the power source is a battery. The battery may be disposable, rechargeable, or take the form of a chargeable capacitor. As the electrical conductor of the strain gauge deforms, as the joint distraction lever deforms as the torque is applied to distract the bones of the joint, the electrical resistance of the electrical conductor of the strain gauge changes. Thus, from the measured electrical resistance of the strain gauge(s), computed using the known or measured input voltage and measured output voltage, the amount of applied stress to the joint distraction lever can be measured and the distraction force computed. A plurality of strain gauges may be arranged and included in the joint distraction lever to form a load cell. The output of the load cell transducer can then be used to convert the force or stress determined by the strain gauges into an electrical signal.

Other mechanisms or tools for measuring the distraction force applied by the joint distraction lever at the distal tip 20 include piezoelectric pressure sensors wherein a charge is generated when a piezoelectric crystal, or other suitable material, of the pressure sensor is stressed. The charge output, or the charge output converted to a voltage signal, for example, may be used to compute and indicate the distraction force being applied by the distraction lever. Similarly, stress to the lever body 12 to compute the distraction force applied at the distal tip 20 can be determined using optical sensors in a cantilever beam configuration. The optical sensors may include an array of optical fibers capable of providing computation of stress and strain by way of wavelength variations between the light source and a detector caused by modifications in the optical fiber body. Finally, a magnetic contact switch may be used to indicate the presence of a load being applied, or can be configured to indicate how much load is being applied.

Figure 7A:
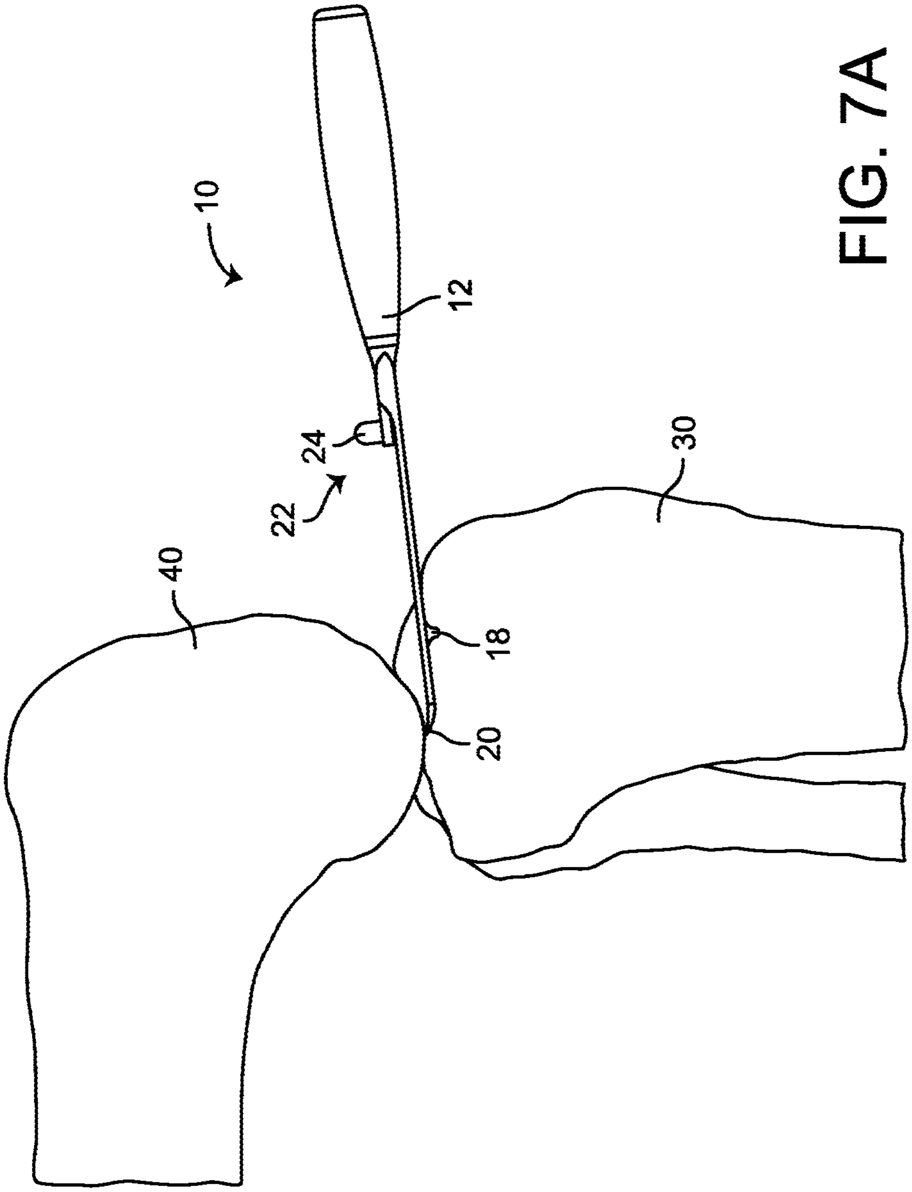
FIGS. 7A-7C depict joint distraction of a patient's knee joint using a joint distraction lever having an indicator according to an exemplary embodiment.
Figure 7B:
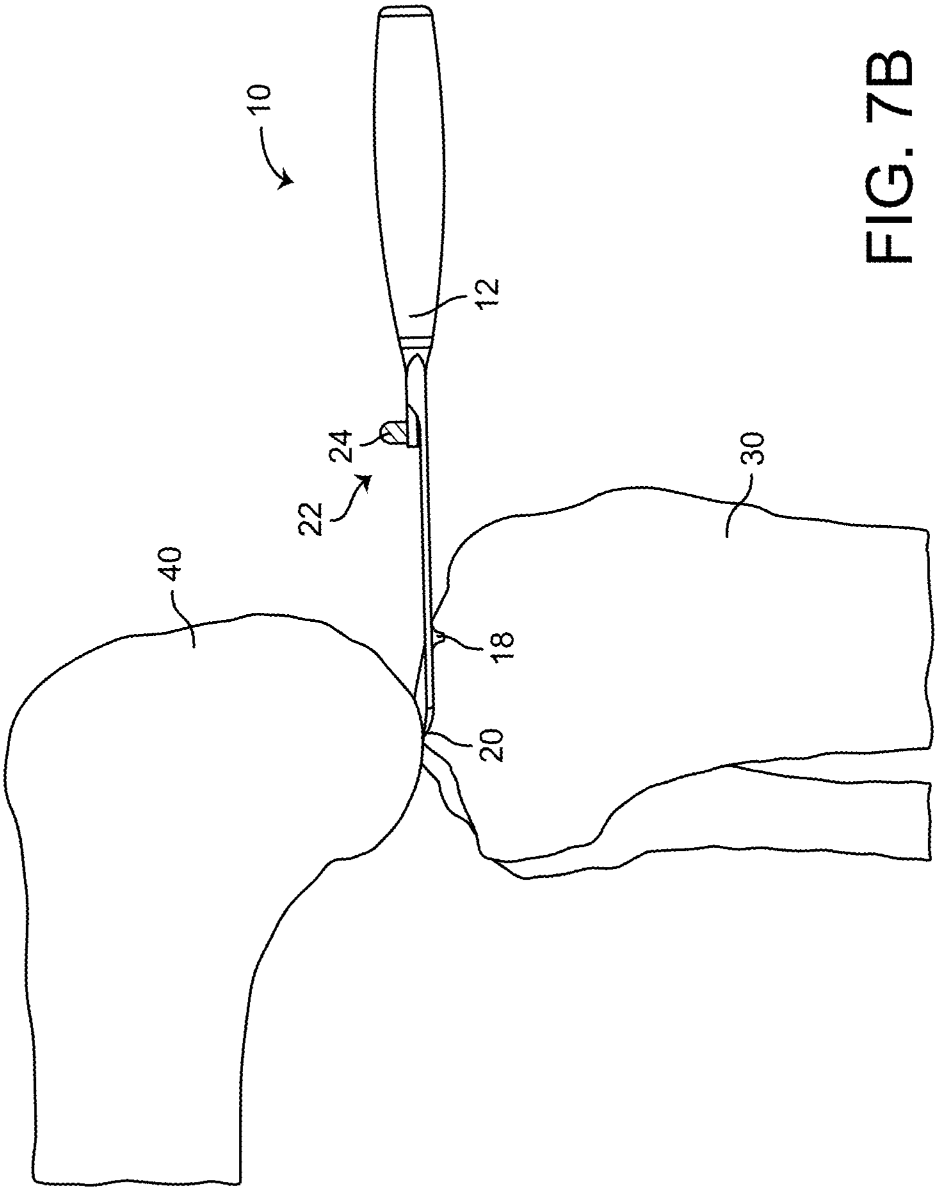
Figure 7C:
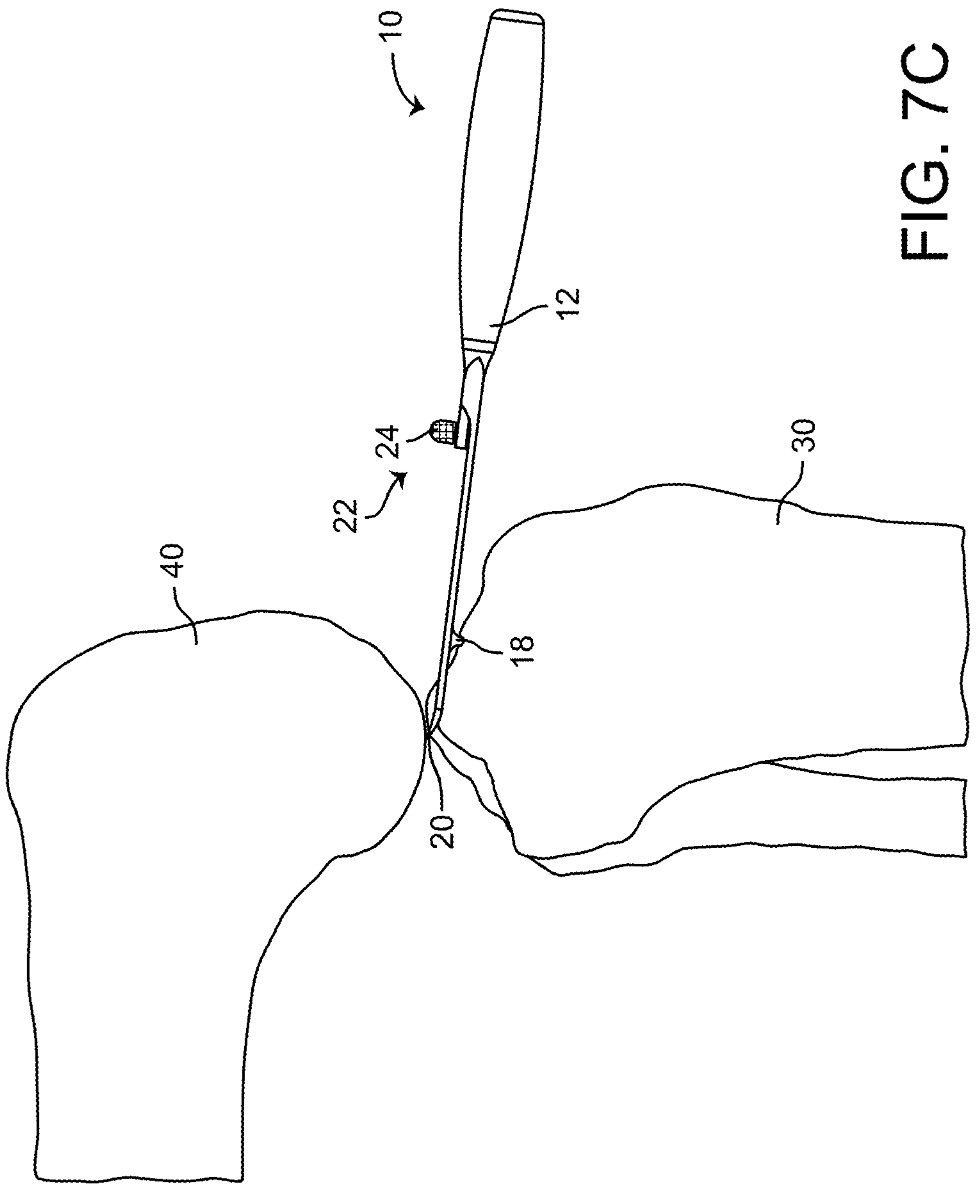

Referring to FIGS. 7A-7C, osteotome 10 includes an indicator 22. The indicator 22 provides feedback to a user related to the distraction force being applied to a first bone of the joint, such as the distal femur, at the distal tip 20. The feedback may indicate the current value of the force being applied, or it may be representative of a particular range of force values, i.e. provide feedback when a predetermined force value has been reached or exceeded. The feedback provided via indicator 22 allows for consistent, repeatable, trainable force application. Distinct from prior methods and systems for joint distraction where force is subjective, changes between surgeons, and is difficult to learn, the joint distraction lever according to the disclosed embodiments provides feedback to the user such that consistent force can be quantified and applied uniformly among different surgeons, between one distraction procedure and the next, and can be applied at any flexion angle. In certain embodiments, the osteotome 10 is configured to apply a force of 85N+/−15N. Accordingly, the indicator 22 is configured to provide feedback to the user when the distraction force achieves some predetermined relationship with the desired force value.

FIGS. 7A-7C depict osteotome 10 having an indicator 22 according to a preferred embodiment, wherein the indicator 22 is a light-emitting diode (LED) 24. As shown in FIG. 7A, the LED 24 is in a first illumination state as a first range of distraction force is being applied. For example, as the osteotome 10 is first inserted in the joint space and no force is being applied, or only a low amount of force is being applied, the LED 24 may emit light of a certain color, or remain off. FIG. 7B depicts the LED 24 in a second state once the distraction force has achieved or passed a certain predetermined value. For example, the second illumination state may cause the LED to emit light of a second color. In an exemplary embodiment, the second state may occur when the distraction force reaches 70N+/−5N. Finally, FIG. 7C depicts the LED 24 in a third illumination state, indicating to the user the a predetermined, desired distraction force, or a maximum distraction force, has been achieved. For example, the LED may emit light of a third color once the predetermined force has been reached. In an exemplary embodiment, the third state may occur when the distraction force reaches 100N+/−5N. Alternatively, the LED may provide other illumination states such as a slow or rapid flashing state to provide an indication that a predetermined force has been reached.

Some embodiments may use a plurality of LEDs. For example, when any force is applied, a first LED may illuminate. Additional LEDs may illuminate successively as the force increases, each illuminating once the force meets a predetermined value. The desired distraction force may be indicated when all of the LEDs on the lever are illuminated.

Similarly, instead of an LED 24, the indicator 22 may provide feedback in the form of a sound emitted from the osteotome, such as a beep or click, or arrangement thereof indicating, for example, a first, second, and third state. Alternatively, the osteotome 10 may provide a single beep, click, or other sound only when the desired, predetermined force value has been reached. Likewise, the indicator 22 may provide feedback in the form of haptic vibration of the joint distraction lever. As with the LED 24 and the sound indicator, the haptic vibration may indicate to a user various of ranges of distraction force being achieved, or provide feedback only at the desired, predetermined distraction force value.

In the mechanical embodiment of FIG. 1, the indicator is the movement of the cantilever beam 8 above the top face 12*a* of the working portion 16, relative to the height of the tab 9 extending from the handle portion 14. In an embodiment wherein the force computation occurs by an analog torque wrench, the indicator 22 is the analog graduations provided. In electronic embodiments, the output of the various strain sensors may be converted into a signal to display a digital representation of the force value on a display window on the lever body 12 itself or on a display or indicator device coupled thereto. The device may further be configured to communicate the computed force wirelessly with an external system which may display the force value on a display device or provide the sound feedback or other indicator to the user of the forces being applied by the joint distraction lever.

In some embodiments, the joint distraction lever may have a preset target distraction force value, and/or preset force values representing the various force stages. In such embodiments, the various indicators indicate when the preset value is reached. In other embodiments, the joint distraction lever may be adjustable. In this way, the surgeon may set the output, i.e., the feedback provided by the indicator, for a selected amount of force. In one example, the surgeon may use the joint distraction lever to first distract the joint. When the surgeon is applying the necessary and desired amount of force to cause distraction of the joint, he or she can set that as the force value that generates a certain output, for example, the force that causes the LED to illuminate. In this way, the same load can be applied consistently and repeatedly by applying a force until that output is again observed. In one exemplary embodiment, shown in FIG. 4, a dial with value hashtags can be adjusted to set the force value and output according to the surgeon's desired load. In other embodiments, an adjustment of the desired or predetermined values can be adjusted via software implemented in the joint distraction lever and/or with the surgical system 900 (described below). Also, referring to FIG. 3C described above, the distance between the fulcrum and tip can be adjusted such that the doctor can adjust the distraction force without adjusting his or her applied force.

Figure 8:
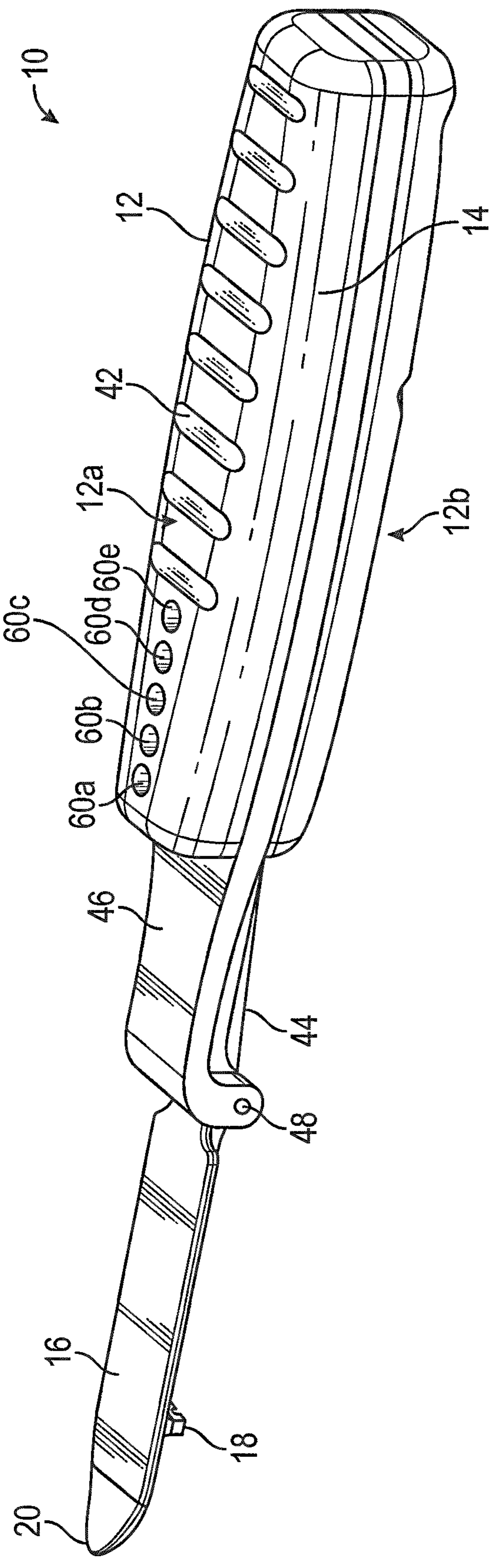
FIG. 8 illustrates a top perspective view of a joint distraction lever, according to another exemplary embodiment.
Figure 9:
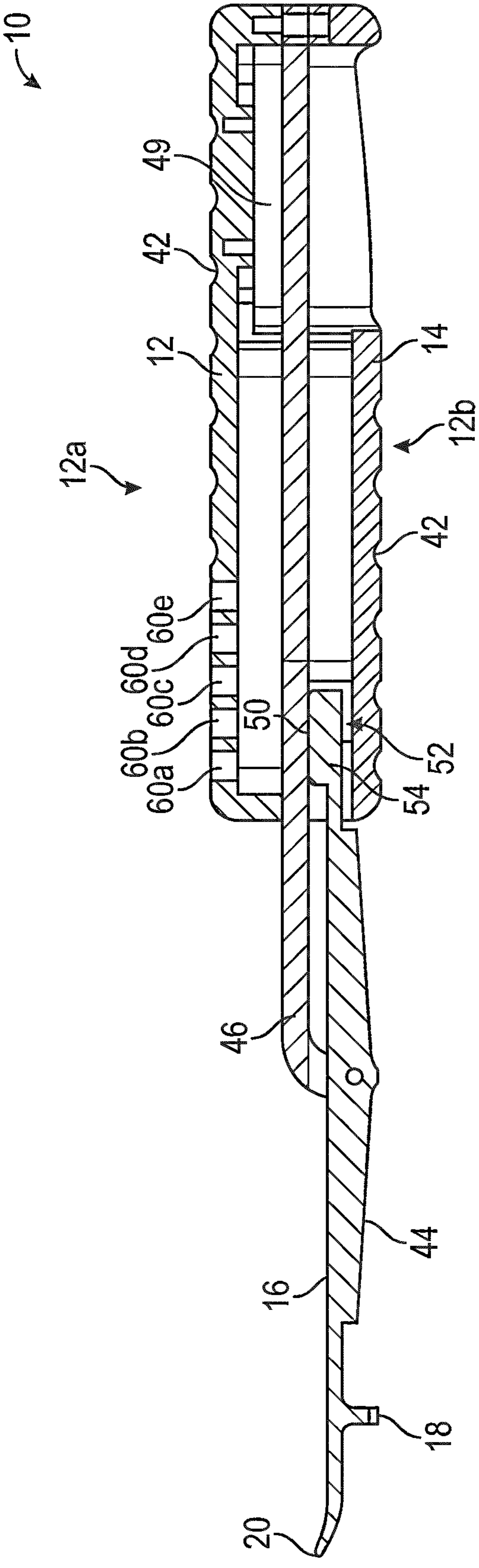
FIG. 9 illustrates a side cross-section of the joint distraction lever of FIG. 8, taken along a lengthwise median line, according to an exemplary embodiment.

Referring now to FIGS. 8 and 9, a joint distraction lever is shown as osteotome 10, according to another exemplary embodiment. FIG. 8 illustrates a top perspective view of the osteotome 10, and the FIG. 9 illustrates a side cross-section of the osteotome 10 taken along a lengthwise median line of the osteotome 10. The osteotome of FIGS. 8 and 9 include similar features as the osteotome 10 of FIGS. 1-7, thus, similar reference numerals are used for similar features.

As shown in FIGS. 8 and 9, in various embodiments, the osteotome 10 includes the lever body 12 having the handle portion 14 and the working portion 16. The fulcrum 18 extends from a bottom face or surface 12*b* of the working portion 16 of the lever body 12. The distal tip 20 is provided at a distal end of the lever body 12. The distal tip 20 is raised to extend above a top face or surface 12*a* of the lever body 12. In the embodiment shown, the distal tip 20 curves upwardly from the working portion 16 at the distal end of the lever body 12. Though the present description will refer to the joint distraction lever as the osteotome 10, however, it is to be understood that the features disclosed herein may be used with and provided in a variety of lever-type devices, which are considered to be within the scope of the present disclosure.

The osteotome 10 has a thin, narrow lever body 12 sized to be inserted into a joint space. In various embodiments, the lever body 12 is between 1-3 mm thick at the working portion 16 and, in certain embodiments, no more than 2 mm thick. Additionally, in some embodiments, the thickness of the working portion 16 tapers towards the distal tip 20 to no more than 1 mm thick at the distal tip 20. The width of the working portion 16 may be between 10-22 mm wide to accommodate compartments of various sizes and, in some embodiments, is approximately 15 mm wide.

The handle portion 14 is configured to be gripped by a user during use of the osteotome 10. As such, the handle portion 14 may be provided with a number of grip grooves 42 on the top face 12*a* and the bottom face 12*b* of the osteotome 10. Although the handle portion 14 is static in the embodiment shown in FIGS. 8 and 9, in some embodiments, the joint distraction lever may have a rotatable handle portion 14. A rotatable handle portion 14 may allow for a reduction in the amount of torque working laterally during joint distraction. For example, when distracting the knee joint, the distraction force should be provided substantially parallel with the mechanical axis of the joint. However, the surgeon may not be able to achieve exact access and grip on the tool such that all forces are being applied in this direction. As a result, some torque may instead be applied sideways on the joint while also being applied in parallel with the mechanical axis. A rotatable handle portion 14 may counteract some of the sideways torque applied by cooperating with the twisting that may occur on the handle when the force is applied at the handle portion 14.

Figure 10:
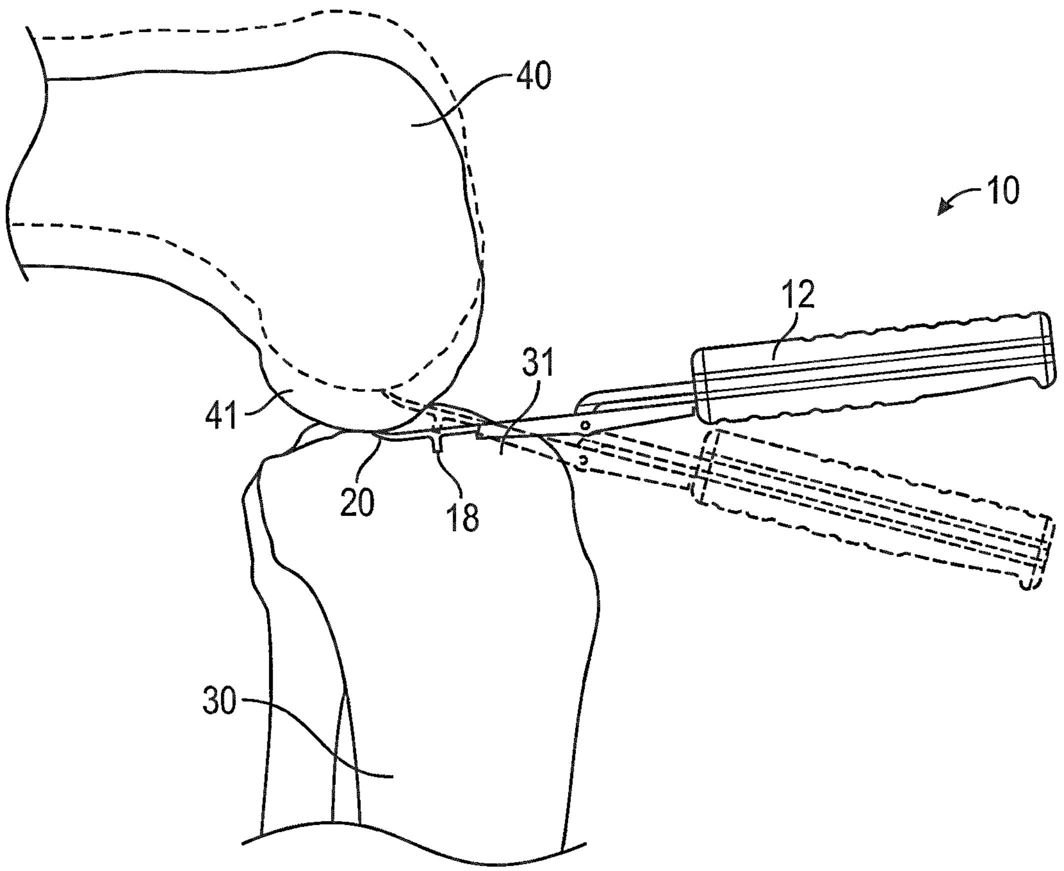
FIG. 10 illustrates the joint distraction lever of FIG. 8 in use during a distraction procedure, according to an exemplary embodiment.

The working portion 16 is configured to transmit a force provided by a user at the handle portion 14 to a bone of a joint. Referring now to FIG. 10, an illustration of the osteotome 10 is shown, according to an exemplary embodiment. As shown in FIG. 10, the fulcrum 18 of the osteotome 10 is configured to rest on a first bone (e.g., a tibial plateau 31 of a patient's tibia 30, as illustrated in FIG. 10) and apply a force to a second bone (e.g., a femoral condyle 41 of a patient's femur 40, as further illustrated in FIG. 10). However, it should be understood that while the embodiments of the joint distraction device are depicted and described herein and being used in a knee joint, the joint distraction device may be used in any joint that is suitable for a joint distraction procedure. Resting the fulcrum 18 on the tibial plateau 31 provides support for the osteotome 10 as a torque is applied at the handle portion 14. The torque is then provided to the femur 40 through the distal tip 20, which is inserted between the tibia 30 and the femur 40. The provided torque causes distraction of the joint (e.g., separation of the first and second bones of the joint), which is shown in FIG. 10 as a separation of the tibia 30 from the femur 40.

Accordingly, the joint distraction device according to various embodiments is dependent on the force being applied at two known locations: the fulcrum 18 and the distal tip 20. To ensure that forces are being applied only at these two locations, the fulcrum 18 and the distal tip 20 project from the bottom face 12*b* and the top face 12*a*, respectively, of the lever body 12 such that the lever body 12 does not inadvertently contact either bone of the joint.

Referring first to the fulcrum 18, the fulcrum 18 is designed to project from the bottom face 12*b* to a distance sufficient to prevent contact of the bottom face 12*b* with the tibia 30 during use. In one embodiment, the fulcrum 18 extends proud of the lever body 12 by at least 2 mm but may be anywhere between 1-3 mm or more proud of the lever body 12. In certain embodiments, the widest portion of the fulcrum 18 is between 4-8 mm, and the thickest portion is between 1-2 mm. The fulcrum may be instrumented such that the fulcrum itself is configured to measure the load being applied at the fulcrum. In such an embodiment, an instrumented fulcrum can be attached to a standard osteotome to achieve certain features of the disclosed embodiments without further modification to force-measuring aspects of the osteotome.

The fulcrum 18 may be designed in various shapes. In one embodiment, the fulcrum 18 is shaped as two "teeth" that extend laterally across the bottom face 12*b* of the working portion 16. The teeth are configured to be sharp enough to "bite" (e.g., penetrate a small distance to hold the osteotome 10 in place) into the bone that the osteotome 10 rests on during the distraction of the joint but not so sharp that the teeth penetrate far into or cause damage to the bone. However, in other embodiments, the fulcrum 18 may be a flat, linear fulcrum, a triangular fulcrum, and so on. Further, in some embodiments, the fulcrum 18 may be connected to the lever body 12 at a rotatable pivot joint.

The distraction force, and thus the measurement of the distraction force applied through the distal tip 20 (to be discussed in detail below) is sensitive to the distance between the fulcrum 18 and the lift point (e.g., distal tip 20 in the embodiment shown in FIGS. 8 and 9). When the distance from the fulcrum 18 to the raised distal tip 20 is known or selected, the applied distraction force can be calculated. Accordingly, the fulcrum 18 may be spaced at a fixed distance from the distal tip 20, or the distance between the fulcrum 18 and the distal tip 20 may be adjustable. In fixed embodiments, the fulcrum-to-tip spacing may be 10-25 mm. In adjustable embodiments, the fulcrum-to-tip spacing may be adjusting by moving the joint of the fulcrum 18 to the lever body 12 along a slot and securing the fulcrum 18 at a desired distance from the distal tip 20. As an example of the fulcrum-to-tip spacing, in one embodiment, the distance between the fulcrum 18 and the distal tip 20 is fixed at 20 mm. This distance is particularly useful for distraction of the knee joint, as it allows the fulcrum 18 to rest on the tibial plateau 31 of the tibia 30 and the distal tip 20 to be directly below the femoral condyle 41.

As shown in FIGS. 8 and 9, the distal tip 20 projects above the top face 12*a* of the lever body 12. For example, in the embodiments shown, the distal tip 20 projects upward in a curve. As discussed above, to ensure that forces are applied to the bones of the joint only at the fulcrum 18 and distal tip 20, the distal tip 20 is configured such that the top face 12*a* of the lever body 12 does not contact the distracted bone, for example, the femur 40, during distraction of the joint. As such, in various embodiments, the raised distal tip 20 stands 1-5 mm proud of the top face 12*a* of the lever body 12 and, in one embodiment, is curved to be 4 mm proud of the lever body 12. The end of the distal tip 20 may be a rounded end, as shown in FIGS. 8 and 9. Alternatively, the lever body 12 may taper towards the distal tip 20 such that distal tip 20 is pointed (e.g., pointed with a width of about 1 mm), is flat, and so on.

While FIGS. 8 and 9 illustrate an exemplary profile of the lever body 12, the lever body 12 of the osteotome 10, and particularly the distal tip 20, may take on other profiles in other embodiments. For example, the distal tip 20 may take on the shape of a plate that is slightly curved to fit with the outer surface of the bone, may be specifically configured for a particular bone or the anatomy of a particular patient, so on. Flatter plate configuration may be advantageous in certain situations by providing greater contact surface area for torque transmission efficiency, as well as reducing penetration of the bone being distracted. Other configurations of the distal tip 20 may also be used in accordance with additional embodiments of the present invention. Additionally, as shown in FIG. 9, the working portion 16 may also include a rib 44 on the bottom face 12*b* configured to strengthen the working portion 16 (e.g., configured to that the osteotome 10 is less likely to break and/or more effectively transmits the force applied at the handle portion 14 to the distal tip 20 during use).

As shown in FIGS. 8 and 9, the handle portion 14 is connected to the working portion 16 by a connecting bar 46. The connecting bar 46 extends through the length of the handle portion 14 and projects from the distal end of the handle portion 14, with the end of the connecting bar 46 curving downward. The working portion 16 attaches to the connecting bar 46 at a hinge 48 provided at the portion of the connecting bar 46 that curves downward. As shown in FIG. 8, the working portion 16 narrows at this connection point to accommodate the hinge 48. The hinge 48 allows the working portion 16 to pivot or rotate during a distraction procedure, which may be used to measure the torque applied during the distraction procedure as discussed in further detail below.

In various embodiments, the joint distraction lever, such as osteotome 10, is configured to measure and provide an output related to the distraction force applied to the bone of the joint by the joint distraction lever during the distraction procedure. The distraction force is measured by a force measurement device, which may be mechanical or electronic.

The embodiment of the osteotome 10 illustrated in FIGS. 8 and 9 includes an electronic force sensor implemented through one or more strain gauges. The one or more strain gauges are configured to receive an input voltage provided by a power source. In certain embodiments, the power source is a battery (e.g., provided in a battery compartment 49 in the handle portion 14 of the osteotome 10, shown in FIG. 9). The battery may be disposable, be rechargeable, or take the form of a chargeable capacitor. Each strain gauge includes an electrical conductor that is configured to deform when provided with a force, such as the torque applied to distract the bones of a joint. As the electrical conductor of the strain gauge deforms, the electrical resistance of the electrical conductor of the strain gauge changes. Thus, from the measured electrical resistance of the strain gauge(s), computed using the known or measured input voltage and measured output voltage, the amount of applied stress to the joint distraction lever can be measured and the distraction force computed.

In various embodiments, a plurality of strain gauges may be arranged and included in the joint distraction lever to form a load cell. The output of the load cell transducer can then be used to convert the force or stress determined by the strain gauges into an electrical signal. In the embodiment shown in FIGS. 8 and 9, the osteotome 10 includes a load cell to measure the distraction force. More specifically, FIG. 9 illustrates a load cell 50 provided within a sensor recess 52 in the handle portion 14. The sensor recess 52 is configured to hold and fully support the load cell 50 within the handle portion 14 and may be, for example, 15.5 mm wide. As further shown in FIG. 9, the proximal end of the working portion 16 extends within sensor recess 52 in the handle portion 14, ending in a sensor indentor 54. The sensor indentor 54 is configured to contact the load cell 50. For example, the sensor indentor 54 may be 13 mm wide such that the surface of the sensor indentor 54 is able to fully contact the load cell 50.

As discussed above, the hinged connection between the handle portion 14 and the working portion 16 at the connecting bar 46 allows the working portion 16 to pivot relative to the handle portion 14 during a distraction procedure. Accordingly, when a torque is applied to the handle portion 14 during a distraction procedure, the sensor indentor 54 pivots upward to contact and deform the load cell 50. The more torque that is applied at the handle portion 14 during the procedure, the more the sensor indentor 54 will deform the load cell 50. The deformation of the load cell 50 may thus be used to measure the amount of applied torque, as discussed above.

Alternatively, in other embodiments, a load cell may be provided at any location on the osteotome. For example, while the embodiment shown in FIGS. 8 and 9 allows for indirect measurement of the applied torque, the applied torque may be more directly measured by locating the load cell, for example, at the distal tip 20 where the torque is applied by the osteotome 10 to the bone of the joint. Furthermore, other electronic mechanisms or tools for measuring the distraction force applied by a joint distraction lever may be used, such as piezoelectric pressure sensors configured to generate a charge when a piezoelectric crystal, or other suitable material, of the pressure sensor is stressed. The charge output, or the charge output converted to a voltage signal, for example, may be used to compute and indicate the distraction force being applied by the distraction lever. Alternatively, stress in the lever body 12 may be determined using optical sensors in a cantilever beam configuration and used to compute the distraction force applied at the distal tip 20. The optical sensors may include an array of optical fibers capable of providing computation of stress and strain by way of wavelength variations between a light source and a detector caused by modifications in the optical fiber body. As yet another alternative, a magnetic contact switch may be used to indicate the presence of a load being applied and/or may be configured to indicate how much load is being applied.

In various embodiments, the osteotome also includes a force value output. In some embodiments, the force value output is one or more indicators on the osteotome. The indicator(s) provide feedback to a user related to the distraction force being applied to a first bone of the joint, such as the femur 40, at the distal tip 20. The feedback may indicate the current value of the force being applied, or the feedback may be representative of a particular range of force values (i.e. provide feedback when a predetermined force value has been reached or exceeded). The feedback provided via the indicator allows for consistent, repeatable, trainable force application. Distinct from prior methods and systems for joint distraction where force is subjective, changes between surgeons, and is difficult to learn, the joint distraction lever according to the disclosed embodiments provides feedback to the user such that consistent force can be quantified and applied uniformly among different surgeons, between one distraction procedure and the next, and at any flexion angle. In certain embodiments, the osteotome 10 is configured to apply a force of 85N+/−15N. Accordingly, the indicator(s) are configured to provide feedback to the user when the distraction force achieves some predetermined relationship with this desired force value.

In FIGS. 8 and 9, the osteotome 10 is provided with an indicator in the form of a series of light-emitting diodes ("LEDs") 60. As shown in FIG. 9, the LEDs 60 are provided within a series of recessed holes within the handle portion 14, though in other embodiments the LEDs 60 may be provided in, for example, a single slot in the handle portion 14. In the embodiment shown in FIGS. 8 and 9, the osteotome 10 is provided with five LEDs 60, shown as LED 60*a*, LED 60*b*, LED 60*c*, LED 60*d*, and LED 60*e*, although it should be understood that the osteotome 10 may be provided with any number of LEDs and/or with any other type of indicator. In various embodiments, the LEDs 60 emit remain off, emit light of a certain color, blink in a predetermined pattern, and so on to indicate to the user the amount of force being applied.

For example, in one embodiment, once a battery is inserted into the battery compartment 49 and/or the osteotome is turned on, the LED 60*a* blinks if no force is currently being applied to the osteotome 10. Once a torque begins to be applied at the distal tip 20, causing the sensor indentor 54 to contact the load cell 50, the LED 60*a* remains constantly lighted. As the torque is increased, the LEDs 60*b*-60*e* light up in succession. When the LEDs 60*a*-60*e* are all constantly lit, this indicates to the user that the desired amount of force is being applied to the osteotome 10 (e.g., the amount of force suited for successfully carrying out the distraction procedure). If additional torque is applied to the osteotome 10, the LEDs 60*a*-60*e* begin to blink, indicating that the user is applying too much torque to the osteotome 10 (e.g., the user is applying an amount of torque that may injure the patient). In this way, the LEDs 60*a*-60*e* aid a user in applying the appropriate amount of force during a distraction procedure such that each distraction procedure may be carried out safely and reliably.

However, it should be understood that this is merely an example of how LEDs 60 may be used to provide feedback to the user during a distraction procedure. Other embodiments of the osteotome 10 may include different numbers of LEDs 60 and/or light the LEDs 60 in a different manner to provide feedback. As another example, the osteotome 10 may instead include a single LED 60. When the osteotome 10 is first inserted in the joint space and no force is being applied, or only a low amount of force is being applied, the LED 60 may emit light of a certain color or remain off. When the distraction force reaches a first level (e.g., 70N+/−5N), the LED 60 may emit light of a second color. When the distraction force reaches a second level (e.g., 100N+/−5N), the LED 60 may emit light of a third color to indicate that a predetermined, desired distraction force, or a maximum safe distraction force, has been applied. Alternatively, the LED 60 may blink at a slow or a rapid flashing state to provide an indication that a predetermined force has been achieved. As a further alternative, the LED 60 may only light up when a predetermined, desired level of force has been achieved.

Figure 11:
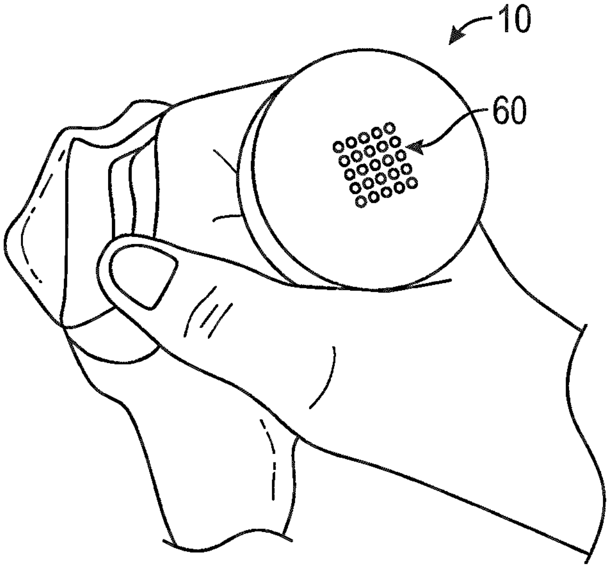
FIGS. 11-13 illustrate the joint distraction lever of FIG. 8 provided with an indicator on the proximal end thereof, according to an exemplary embodiment.
Figure 12:
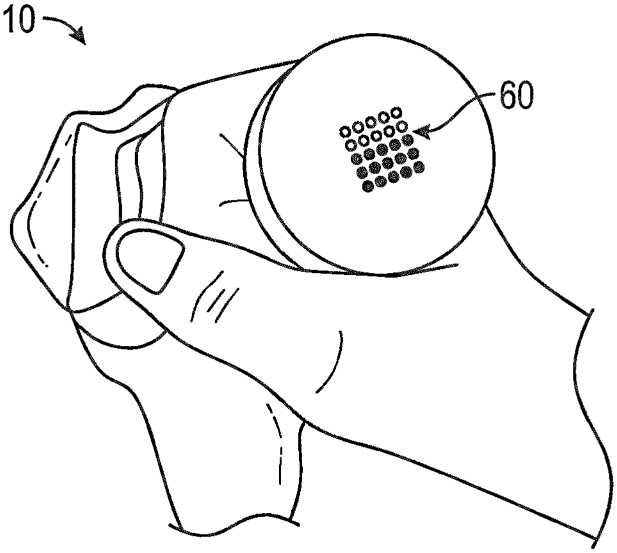
Figure 13:
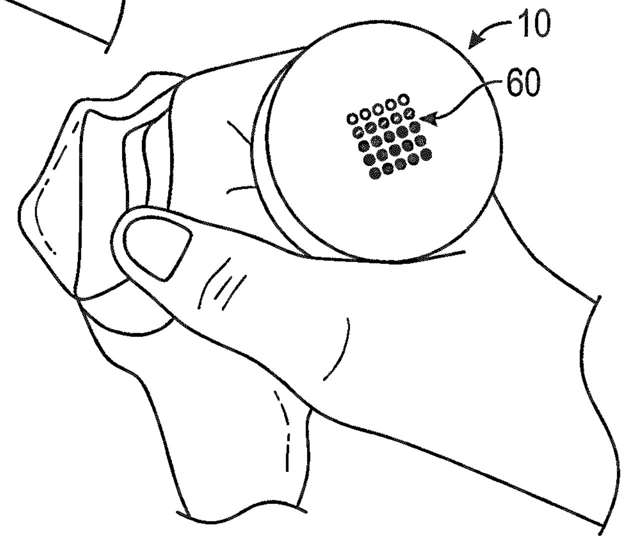

Additionally, it should be understood that an indicator may be provided on any part of the osteotome 10. Referring now to FIGS. 11-13, an osteotome 10 with LEDs 60 provided on a distal end thereof is shown, according to an exemplary embodiment. In FIG. 11, no force has been applied to the osteotome 10, and accordingly the LEDs 60 are off. As increasing force is applied to the osteotome 10, the bottom three LEDs 60 light up sequentially from bottom to top. When the user has applied a desirable amount of force to the osteotome 10, all three bottom LEDs 60 are lit (e.g., lit in a green light), as shown in FIG. 12. However, as shown in FIG. 13, if the user continues to apply force to the osteotome 10, the fourth LED 60 and eventually the fifth and top LED 60 light up (e.g., with the fourth LED 60 lit in a yellow light and the fifth LED 60 lit in a red light) to indicate to the user that the user is applying too much force for the procedure.

It should further be understood that, while the indicator in FIGS. 8-13 is shown as LEDs 60, in other embodiments an indicator may be provided differently. In one embodiment, the osteotome 10 may instead include a sound device (e.g., a speaker system) configured to emit sound, such as a beep or click, or an arrangement of sounds indicating different force states. In another embodiment, the osteotome 10 may include a haptic feedback device configured to provide feedback in the form of haptic vibration of the osteotome 10. The haptic vibration may also indicate to a user various of ranges of distraction force being achieved by the osteotome 10 (e.g., by providing different amounts of vibration based on the magnitude of the distraction force) or provide feedback only at the desired, predetermined distraction force value.

In some embodiments, an indicator for the joint distraction lever may have a preset target distraction force value and/or preset force values representing the various force stages (e.g., different force values associated with a green light and a red warning light). In other embodiments, the indicator for the joint distraction lever may have adjustable force values. In this way, the surgeon may set the output (e.g., the feedback provided by the indicator) for a selected amount of force. For example, a dial with value hashtags may be adjusted to set the force value and/or type of output according to the surgeon's desired load. As another example, an adjustment of the desired or predetermined values may be adjusted via software implemented in the joint distraction lever and/or via the surgical system 900 described below with reference to FIG. 15. As an illustration, the surgeon may use the joint distraction lever to first distract a joint. When the surgeon is applying the necessary and desired amount of force to cause distraction of the joint, he or she can set that as the force value for generating a certain output in the osteotome 10 (e.g., the force that causes the LED to illuminate). In this way, the same load can be applied consistently and repeatedly by the user applying a force until that output is again observed. Furthermore, as described above, in some embodiments, the distance between the fulcrum and the tip of the joint distraction lever may be adjustable such that a user may adjust the distraction force by changing the distance between the fulcrum and the tip.

In embodiments of the osteotome 10 including an electronic force measurement device, the force value output may be a signal to display a digital representation of the force value on a display window provided on the lever body 12 itself or on a display or indicator device coupled to the lever body 12. Alternatively, or additionally, the osteotome 10 may be configured to communicate the computed force wirelessly with an external system (e.g., an external computing system). As such, the osteotome 10 may include a communications device or network interface such that the osteotome 10 is able to communicate with the external system via Bluetooth, RFID, Wi-Fi, etc. The external system may display the force value on a display device, provide sound feedback, or provide another indicator to the user of the forces being applied by the joint distraction lever based on data, received from the osteotome 10, relating to the distraction force applied by the osteotome 10.

Furthermore, the external system may include software (e.g., implemented as instructions stored in a non-transitory machine-readable medium or memory, the instructions executable by a processor), such as a robotic balancing application, configured to guide the user in performing the distraction procedure or, more broadly, a joint resection. In various embodiments, the external system may communicate with the joint distraction lever to facilitate the distraction procedure. For example, in one embodiment, the external system may identify a stiffness transition point (e.g., the point where a ligament transitions from low stiffness to high stiffness) using an output from the osteotome 10, such as an output of the force measurement device, or using an output from another device or devices. In another embodiment, the osteotome 10 may include a button (e.g., provided on the lever body 12) that the user may push to collect pose data for the resection joint, as described in further detail below with reference to FIGS. 14 and 15. Further, the external system may wirelessly receive, process, and display the pose data to the user. In various arrangements, the external system is implemented as the surgical system 900, which is described in further detail below with reference to FIG. 15.

In some embodiments, the joint distraction lever is implemented as a single joint distraction lever, as illustrated by the osteotome 10 shown in FIGS. 8-13. Such an embodiment of the osteotome 10 may be used in either a partial knee arthroplasty ("PKA") or a total knee arthroplasty ("TKA"). In other embodiments, the joint distraction lever is implemented as a dual joint distraction lever. As an example, the joint distraction lever may be implemented as an dual compartment osteotome with two working portions connected to a single handle, with the two working portions configured to be inserted on both sides of a joint (e.g., on the medial and lateral sides of a knee joint). Such a dual compartment osteotome may be used in a TKA and may be preferable, for example, by decreasing the amount of force the surgeon must apply to distract the joint.

Figure 14:
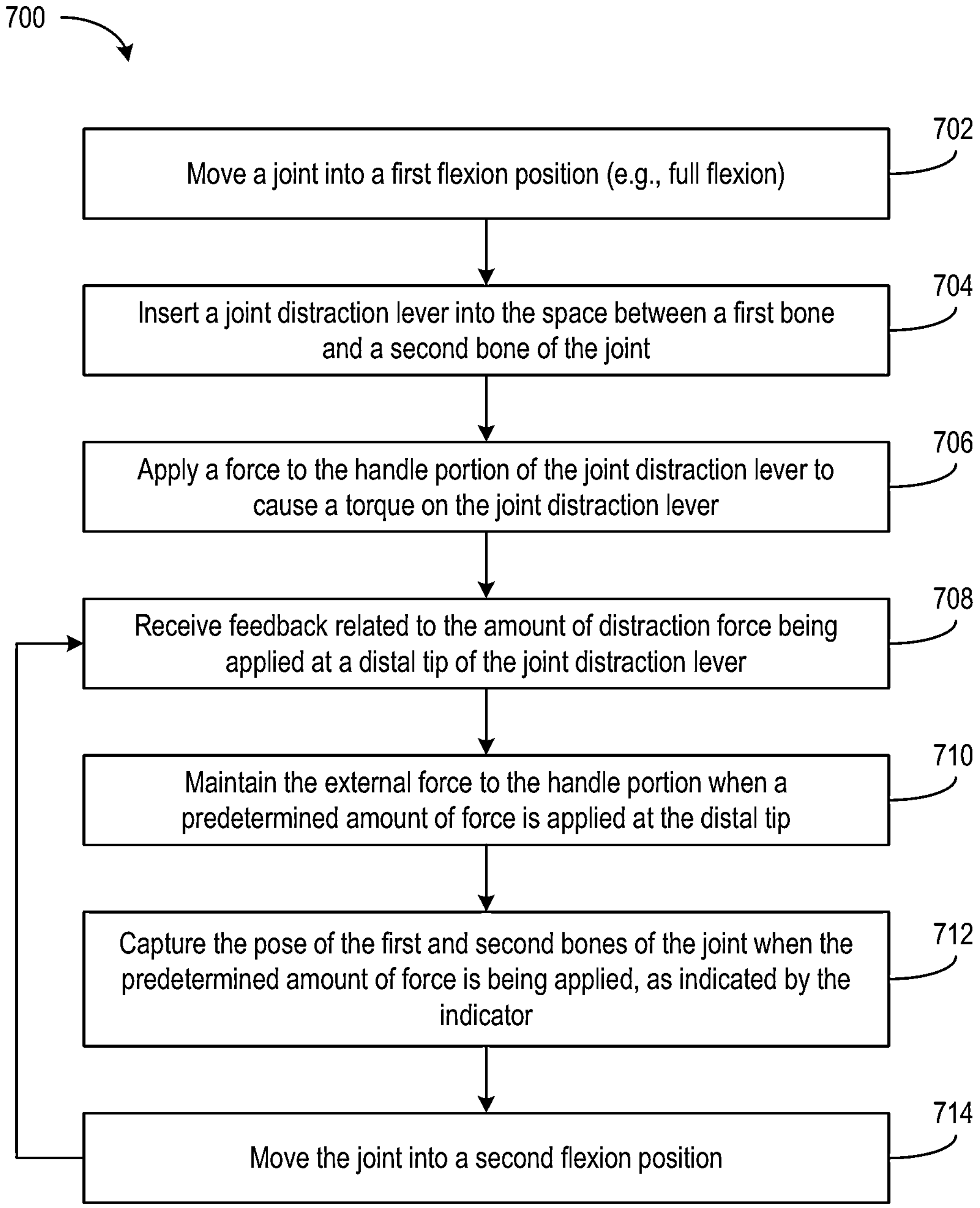
FIG. 14 illustrates a method of carrying out a distraction procedure using a joint distraction lever, according to an exemplary embodiment.

Referring to FIG. 14, a method 700 for performing a joint distraction using a joint distraction lever is depicted, according to an exemplary embodiment. A joint, such as the knee joint including the tibia 30 and the femur 40, is first moved into a first flexion position (step 702). For example, the first flexion position is full flexion though any range of flexion.

A joint distraction lever, such as the osteotome 10, is then inserted into the space between a first bone and a second bone of the joint (step 704). An external force is then applied to the handle portion 14 of the lever body 12 to cause a torque on the joint distraction lever (step 706). As a result, the user receives feedback related to the amount of distraction force being applied to the first or the second bone of the joint at the distal tip 20 of the joint distraction lever, as measured by components of the joint distraction lever (e.g., a force measurement device, such as load cell 50, etc.) (step 708). After having achieved a predetermined amount of force at the distal tip 20, and being aware of that the predetermined amount of force is being applied by the feedback, the user maintains the external force to the handle portion 14 to complete the joint distraction procedure (step 710).

Figure 15:
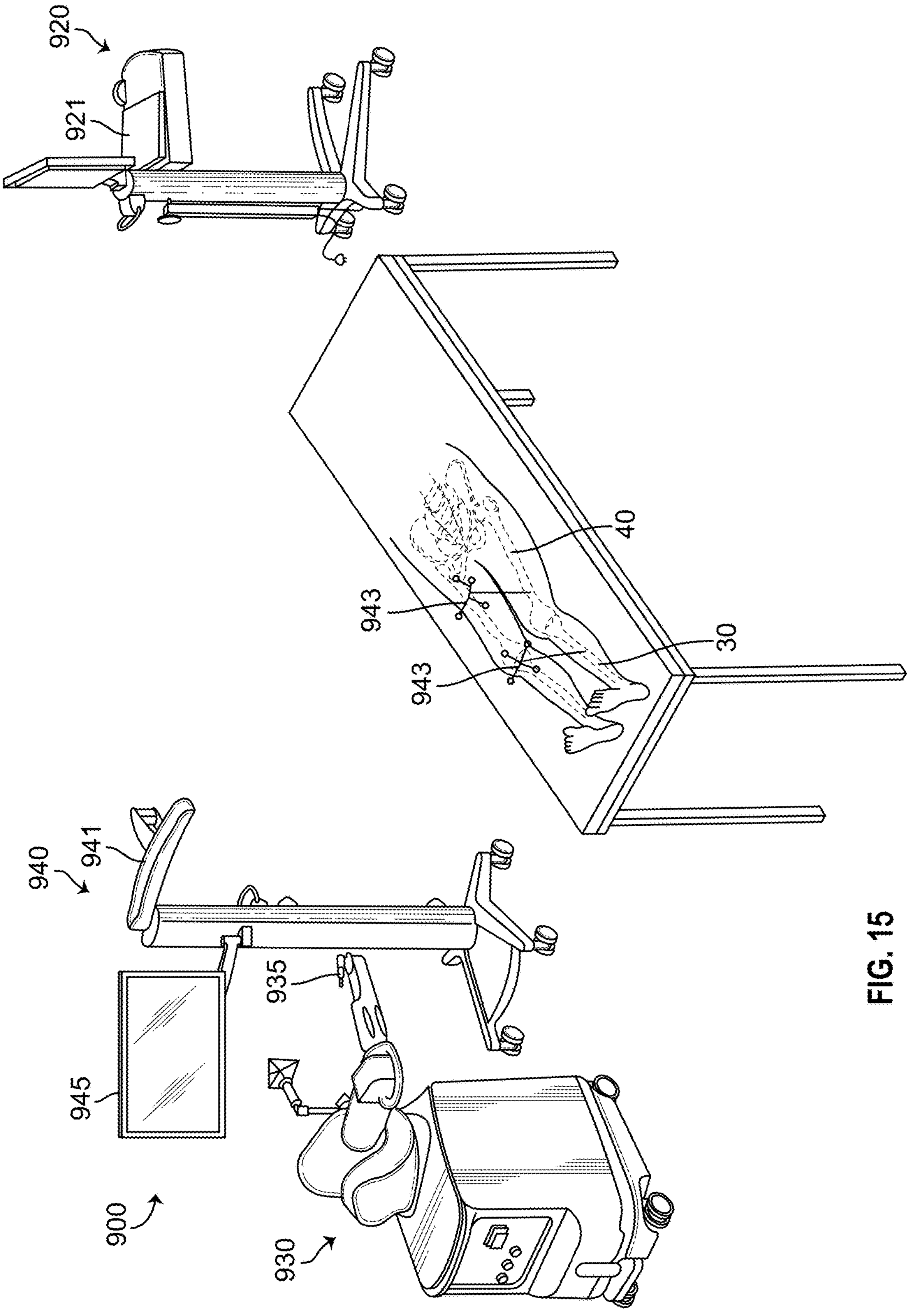
FIG. 15 illustrates a surgical system configured to be used with a joint distraction lever, according to an exemplary embodiment.

Optionally, after step 710, a pose of the first and second bones of the joint is captured when the predetermined distraction force is applied and maintained at the distal tip 20 (step 712). Capturing the pose of the first and second bones in the distracted joint assists with surgical planning to ultimately attain the desired, properly aligned joint post-resection and post-prosthetic implantation. To provide for capturing the pose of the joint, the joint distraction lever may be used in conjunction with anatomy navigation systems and methods, which may further be used with a surgical system, such as those depicted in FIG. 15. FIG. 15 illustrates a surgical system 900 that includes a computing system 920, a surgical tool such as haptic device 930, and a tracking system 940. In operation, the surgical system 900 enables comprehensive surgical planning, which may include performing distraction of a joint using the osteotome 10 described herein.

Determining the pose of the first and second bones in step 712 may make use of the tracking system 940. The tracking (or localizing) system 940 of the surgical system 900 is configured to determine a pose (i.e., position and orientation) of one or more objects during a surgical procedure to detect movement and capture poses of the object(s). For example, the tracking system 940 may include a detection device 941 that obtains a pose of an object with respect to a coordinate frame of reference of the detection device. As the object moves in the coordinate frame of reference, the detection device 941 tracks the pose of the object to detect (or enable the surgical system 900 to determine) movement of the object. Tracked objects may include, for example, tools/instruments, patient anatomy, implants/prosthetic devices, and components of the surgical system 900. Using pose data from the tracking system 940, the surgical system 900 is also able to register, map, or associate coordinates in one space to those in another to achieve spatial alignment or correspondence (e.g., using a coordinate transformation process as is well known). Objects in physical space may be registered to any suitable coordinate system, such as a coordinate system being used by a process running on the computer 921.

For example, utilizing pose data from the tracking system 940, the surgical system 900 is able to associate the physical anatomy with a representation of the anatomy (e.g., an image displayed on a display device 945). Based on tracked object and registration data, the surgical system 900 may determine, for example, a spatial relationship between the image of the anatomy and the relevant anatomy. Additionally, by tracking the relevant anatomy, the surgical system 900 can compensate for and ascertain movement of the relevant anatomy during the surgical procedure, as needed for capturing the pose of the distracted joint at the flexion position.

Registration may include any known registration technique, such as, for example, image-to-image registration (e.g., monomodal registration where images of the same type or modality, such as fluoroscopic images or MR images, are registered and/or multimodal registration where images of different types or modalities, such as MRI and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MRI images to an intraoperative scene).

The tracking system 940 may also be used to track the anatomy and the joint distraction lever, or osteotome 10, while applying the distraction force. By tracking the pose (i.e., position and orientation) and the movement of the osteotome 10 and the anatomy, the computing system 920 may determine the directional components of the force being produced. As described above, in addition to the forces acting along the mechanical axis of the bone being moved, the distraction force may also act in a lateral direction or other direction off-axis from the mechanical axis. Tracking of the objects used during a distraction procedure and determination of the directional components may allow for a determination of the amount of force that is off of the intended axis. This may help the surgeon adjust the application of force for more efficient load transmission and/or to reduce any injury or damage that may occur may applying distraction forces in directions that are off of the intended axis. Alternatively, the surgical system 900 may be configured to adjust the application of force automatically (e.g., by the computing system 920 or the haptic device 930 providing haptic feedback to the osteotome 10 during the distraction procedure).

The tracking system 940 may be any tracking system that enables the surgical system 900 to continually determine (or track) a pose of the relevant anatomy of the patient and a pose of the surgical tool 935 (and/or the haptic device 930). For example, the tracking system 940 may comprise a non-mechanical tracking system, a mechanical tracking system, or any combination of non-mechanical and mechanical tracking systems suitable for use in a surgical environment.

A non-mechanical tracking system may include, for example, an optical (or visual), magnetic, radio, or acoustic tracking system. Such systems may include a detection device adapted to locate, in a predefined coordinate space, specially recognizable trackable elements ("trackers") that are detectable by the detection device and that are either configured to be attached to the object to be tracked or are an inherent part of the object to be tracked. For example, a trackable element may include an array of markers having a unique geometric arrangement and, when attached to the tracked object (e.g., the femur 40 and tibia 30 of a patient), a known geometric relationship to the tracked object. These markers may include any known marker, such as extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device 941. Intrinsic features are salient and accurately locatable portions of the tracked object that are sufficiently defined and identifiable to function as recognizable markers for the detection device 941 on their own (e.g., landmarks, outlines of anatomical structure, shapes, colors, or any other sufficiently recognizable visual indicator).

The markers may be located using any suitable detection method, such as, for example, optical, electromagnetic, radio, or acoustic methods as are well known. For example, an optical tracking system having a detection device 941 implemented as stationary stereo camera pair sensitive to infrared radiation may be used to track markers that emit infrared radiation either actively (e.g., as LEDs) or passively (e.g., spherical markers with surfaces that reflect infrared radiation). Similarly, a magnetic tracking system may include a stationary field generator that emits a spatially-varying magnetic field sensed by small coils integrated into the tracked object.

In the embodiment shown in FIG. 15, the tracking system 940 includes a non-mechanical tracking system. In this embodiment, the non-mechanical tracking system is an optical tracking system that includes a detection device 941 and at least one tracker, such as trackers 943, configured to be disposed on, or incorporated into, a tracked object and detected by the detection device 941. The trackers 943 are configured to be affixed to the tracked object in a secure and stable manner (e.g., to the tibia 30 and the femur 40, as shown in FIG. 15), and each tracker 943 includes an array of markers having a known geometric relationship to the tracked object. As described above, the markers may be active (e.g., LEDs) or passive (e.g., reflective spheres, a checkerboard pattern, etc.). In some arrangements, the markers may more specifically have a unique geometry (e.g., a unique geometric arrangement of the markers) or, in the case of active, wired markers, a unique firing pattern. In operation, the detection device 941 detects the positions and orientations of the markers (e.g., including the unique geometry or firing pattern) and use a known geometric relationship to the tracked object enable the surgical system 900 to calculate a pose of the tracked object based on the positions of the markers.

As stated above, a virtual representation of the anatomy, such as the knee joint, can be displayed on display device 945. The display device 945 may also display the distraction force measurement obtained by a force measurement device of the joint distraction lever. For example, as described above, the osteotome 10 may communicate wirelessly (e.g., Bluetooth, RFID, etc.) or via a coupled connection with the surgical system 900 to provide the distraction force measurement for display on an external device, such as the display device 945. Furthermore, as also described above, the osteotome 10 may include a button in response to which the surgical system 900 captures the pose of the joint using the tracking system 940 (e.g., because pressing the button causes the osteotome 10 to transmit a command to the surgical system 900 to capture the pose of the joint). The surgical system 900 may further display pose information on the display device 945 and/or use the pose information to complete a surgical planning procedure.

Accordingly, in various embodiments, the computing system 920 may be configured to acquire and use the data obtained during a joint distraction procedure, including pose information (e.g., captured in response to the user pressing a button on the osteotome 10), to complete a surgical planning procedure. Thus, computing system 920 may capture and store the pose of the first and second bones of the joint based on information captured and provided by tracking system 940. For example, the captured pose of the joint may be used to plan bone resection and prosthetic implant placement for proper joint balance and alignment. The computing system 920 of surgical system 900 may be further configured to define a surgical plan based on the captured pose(s) of the distracted joint. The surgical system 900 may then implement the surgical plan, for example, by using the tracking system 940 to track the pose of a surgical tool relative to the patient's anatomy and providing haptic feedback through the haptic device 930 (e.g., based on a position and orientation of a surgical tool 935 relative a haptic boundary created during surgical planning). The haptic feedback provided by the haptic device 930 provides surgical guidance to a surgeon in order to keep the surgical tool 935 from deviating from the surgical plan created based on the joint distraction procedure and other aspects of surgical planning.

Moreover, the computing system 920 may provide surgical guidance to a surgeon during the joint distraction procedure. For example, the computing system 920 may identify a stiffness transition point for the joint (e.g., based on pose information captured by the tracking system 940, based on pre-operative scans of the patient anatomy, based on force information transmitted to the computing system 920 by the osteotome, etc.). The computing system 920 may then provide guidance to the surgeon by, for example, displaying the stiffness transition point on a representation of the patient anatomy via the display device 945.

U.S. Pat. No. 8,010,180, titled "Haptic Guidance System and Method," granted Aug. 30, 2011, which is hereby incorporated by reference herein in its entirety, describes an exemplary surgical system with which the presently described joint distraction lever may be used during a joint distraction procedure and for bone resection and implant planning.

Referring back to the method depicted in FIG. 14, after step 712, the joint is optionally moved to a second flexion position (step 714) and may further be moved to any number of additional flexion positions. In moving the joint to a subsequent flexion position, the user again receives feedback related to the amount of distraction force being applied at the distal tip 20 of the joint distraction lever and maintains the external force to the handle portion 14 when a predetermined amount of force is applied at the distal tip 20 (e.g., determined based on the feedback). Additionally, the poses of the subsequent flexion positions may captured with the predetermined resection force applied to the joint.

In various arrangements, these poses of the flexion position(s), with the predetermined distraction force applied, represent the desired post-resection final position of the joint (e.g., the knee joint). Accordingly, after collecting the poses, bone resection, implant positioning, and implant characteristics are planned (e.g., using the computing system 920) so as to maintain this relative alignment by making the femoral and tibial components contact or be slightly gapped to allow for some laxity. Once the bone is resected at this desired plan and the trials and/or implants are secured to the bone, the leg will be in the desired pre-resected posed positions.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

The invention includes methods that may be performed using the subject devices. The methods may include the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

What is claimed is:

1. A surgical system, comprising:

a joint distractor configured to apply a distraction force to a first bone in contact with the joint distractor to distract a joint;

a tracking system configured to track relative poses of the joint distractor and the first bone of the joint;

a computing system programmed to:

receive information indicating the relative poses of the joint distractor and the first bone of the joint;

determine, using the relative poses of the joint distractor and the first bone of the joint, a component of the distraction force in a lateral direction of the joint; and cause, using the component of the distraction force in the lateral direction of the joint, an adjustment of direction of the distraction force.

2. The surgical system of claim 1, wherein the computing system is configured to receive the information indicating the relative poses of the joint distractor and the first bone of the joint while the joint distractor is applying the distraction force to the joint.

3. The surgical system of claim 1, wherein the adjustment reduces load transmitted in a direction off an intended axis for the distraction force.

4. The surgical system of claim 1, wherein the computing system is programmed to cause the adjustment by providing haptic feedback via the joint distractor.

5. The surgical system of claim 1, wherein the component is an amount of the distraction force that is offset from a mechanical axis of the joint.

6. The surgical system of claim 1, wherein the computing system is configured to cause the adjustment of the distraction force via a robot.

7. The surgical system of claim 1, wherein the adjustment of the direction of the distraction force is automatic.

8. A system, comprising:

a joint distractor configured to apply a distraction force to distract a joint; and an optical tracking system configured to track relative poses of the joint distractor, a first bone of the joint, and a second bone of the joint; and a computing system programmed to:

receive information indicating the relative poses of the joint distractor, the first bone of the joint, and the second bone of the joint;

determine, using the relative poses of the joint distractor and at least one of the first bone of the joint or the second bone of the joint, an amount of the distraction force off of an axis of the joint; and cause, using the amount of the distraction force off of an axis of the joint, an adjustment of direction of the distraction force.

9. The system of claim 8, wherein the computing system is configured to receive the information indicating the relative poses of the joint distractor, the first bone of the joint, and the second bone of the joint while the joint distractor is applying the distraction force to the joint.

10. The system of claim 8, wherein the amount is a directional component of the distraction force which points in a lateral direction of the joint.

11. The system of claim 8, wherein the axis is the mechanical axis of the joint.

12. The system of claim 8, wherein the adjustment reduces load transmitted between the first bone and the second bone off of the axis.

13. The system of claim 8, wherein the computing system is configured to cause the adjustment of the distraction force via a robot.

14. The system of claim 8, wherein the computing system is configured to cause the adjustment of the distraction force by providing haptic feedback via the joint distractor.

15. A system, comprising:
- a joint distractor configured to apply a distraction force to distract a joint;
- a tracking system configured to track relative poses of the joint distractor and a first bone of the joint in contact with the joint distractor; and
- a computing system programmed to:
  - receive information indicating the relative poses of the joint distractor and the first bone of the joint;
  - determine, using the relative poses of the joint distractor and the first bone of the joint, an amount of the distraction force off of a mechanical axis of the first bone; and
  - cause, using the amount, an adjustment of a distraction the distraction force.

16. The system of claim 15, wherein the computing system is configured to receive the information indicating the relative poses of the joint distractor and the first bone of the joint, while the joint distractor is applying the distraction force to the joint.

17. The system of claim 15, wherein the amount is a directional component of the distraction force which points in a lateral direction of the joint.

18. The system of claim 15, wherein the adjustment reduces the amount of the distraction force that is off of the mechanical axis.

19. The system of claim 15, wherein the adjustment adjusts the direction toward the mechanical axis.

20. The system of claim 15, wherein the computing system is configured to cause the adjustment of the distraction force via a robot.

* * * * *